US011183271B2

(12) United States Patent
Frey et al.

(10) Patent No.: US 11,183,271 B2
(45) Date of Patent: *Nov. 23, 2021

(54) NEURAL NETWORK ARCHITECTURES FOR LINKING BIOLOGICAL SEQUENCE VARIANTS BASED ON MOLECULAR PHENOTYPE, AND SYSTEMS AND METHODS THEREFOR

(71) Applicant: Deep Genomics Incorporated, Toronto (CA)

(72) Inventors: Brendan Frey, Toronto (CA); Andrew Delong, Toronto (CA)

(73) Assignee: Deep Genomics Incorporated, Toronto (CA)

( * ) Notice: Subject to any disclaimer, the term of this patent is extended or adjusted under 35 U.S.C. 154(b) by 656 days.

This patent is subject to a terminal disclaimer.

(21) Appl. No.: 15/841,106

(22) Filed: Dec. 13, 2017

(65) Prior Publication Data

US 2018/0165412 A1 Jun. 14, 2018

Related U.S. Application Data

(63) Continuation of application No. PCT/CA2016/050689, filed on Jun. 15, 2016, which
(Continued)

(51) Int. Cl.
*G16B 30/00* (2019.01)
*G16B 40/00* (2019.01)
(Continued)

(52) U.S. Cl.
CPC .............. *G16B 30/00* (2019.02); *G06N 3/04* (2013.01); *G16B 40/00* (2019.02); *G16B 20/00* (2019.02)

(58) Field of Classification Search
CPC ........ G16H 50/20; G16H 10/60; G16H 50/50; G16H 50/70; G16H 50/30; G16H 10/40;
(Continued)

(56) References Cited

U.S. PATENT DOCUMENTS 6,128,609 A * 10/2000 Rose ..................... G06N 3/08
706/25
8,697,359 B1  4/2014 Zhang
(Continued)

FOREIGN PATENT DOCUMENTS

WO    WO-9412948 A1    6/1994
WO    WO-2004048511 A2    6/2004
(Continued)

OTHER PUBLICATIONS

Kolekar et al. alignment-free distance measure based on return time distribution for sequence analysis: applications to clustering, molecular phylogeny and subtyping. (2012) Molecular phylogenetics and Evolution. vol. 65, pp. 510-522. (Year: 2012).*
(Continued)

*Primary Examiner* — Mary K Zeman
(74) *Attorney, Agent, or Firm* — Wilson Sonsini Goodrich & Rosati

(57) ABSTRACT

We describe a system and a method that ascertains the strengths of links between pairs of biological sequence variants, by determining numerical link distances that measure the similarity of the molecular phenotypes of the variants. The link distances may be used to associate knowledge about labeled variants to other variants and to prioritize the other variants for subsequent analysis or interpretation. The molecular phenotypes are determined using a neural network, called a molecular phenotype neural network, and may include numerical or descriptive attributes, such as those describing protein-DNA interactions, protein-RNA
(Continued)

interactions, protein-protein interactions, splicing patterns, polyadenylation patterns, and microRNA-RNA interactions. Linked genetic variants may be used to ascertain pathogenicity in genetic testing, to identify drug targets, to identify patients that respond similarly to a drug, to ascertain health risks, or to connect patients that have similar molecular phenotypes.

24 Claims, 16 Drawing Sheets

Related U.S. Application Data is a continuation-in-part of application No. 14/739,432, filed on Jun. 15, 2015, now Pat. No. 10,185,803.

(51) Int. Cl.
*G06N 3/04* (2006.01)
*G16B 20/00* (2019.01)

(58) Field of Classification Search
CPC ........ G16H 15/00; G16H 70/60; G16B 20/00; G16B 40/00; G16B 50/00; G16B 5/00; G16B 30/00; G16B 40/20; G16B 20/20; G16B 20/40; G16B 40/30; G16B 45/00; G16B 99/00; G16B 25/10; G16B 10/00; G16B 30/10; G16B 20/10; G16B 25/20; G16B 50/10; G16B 50/50; G06F 17/11; G06F 16/285; G06F 16/288; G06F 16/334; G06F 16/3347; G06F 16/353; G06F 19/00; G06F 19/18; G06F 19/20; G06N 5/022; G06N 3/0445; G06N 3/08; G06N 7/005; G06N 20/10; G06N 3/02; G06N 3/04; G06N 3/084; G06N 20/00; G06N 20/20; G06N 3/0454; G06N 5/04; G06N 5/003; G06N 5/02; G06N 3/0427; G06N 3/0472; G06N 5/025; G06N 5/046; C12Q 2600/156; C12Q 1/6883; C12Q 1/6827; C12Q 2537/165; G01N 2800/56; G01N 2800/52; G01N 2570/00; G01N 2800/60; G06T 2207/20084; G06T 2207/20081; G06K 9/6256; G06K 9/6274; G06K 9/6215; G06K 9/6218; G06K 9/6227; G06K 9/6257; G06K 9/6262; G06K 9/6265; G06K 9/6272; G06K 9/6276; G06K 9/628; G16C 20/80
See application file for complete search history.

(56) References Cited

U.S. PATENT DOCUMENTS

| | | | |
|---|---|---|---|
| 9,406,017 B2 | 8/2016 | Hinton et al. | |
| 9,740,817 B1* | 8/2017 | Fernandez | G16H 10/20 |
| 9,922,285 B1* | 3/2018 | Glode | G06N 5/04 |
| 10,185,803 B2 | 1/2019 | Frey et al. | |
| 10,410,118 B2 | 9/2019 | Xiong et al. | |
| 2003/0122816 A1* | 7/2003 | Yu | G06T 17/30 |
| | | | 345/419 |
| 2006/0122816 A1* | 6/2006 | Schadt | G16B 20/00 |
| | | | 703/11 |
| 2008/0030797 A1* | 2/2008 | Circlaeys | H04N 19/12 |
| | | | 358/448 |
| 2008/0300797 A1 | 12/2008 | Tabibiazar et al. | |
| 2011/0010099 A1* | 1/2011 | Adourian | G16B 5/00 |
| | | | 702/19 |
| 2011/0172929 A1* | 7/2011 | Califano | G16B 20/00 |
| | | | 702/20 |
| 2011/0307228 A1* | 12/2011 | Kasabov | G06Q 10/04 |
| | | | 703/2 |
| 2012/0310539 A1 | 12/2012 | Crockett et al. | |
| 2013/0096838 A1 | 4/2013 | Fairbrother | |
| 2013/0332081 A1 | 12/2013 | Reese et al. | |
| 2014/0011977 A1 | 1/2014 | Krainer et al. | |
| 2014/0046696 A1* | 2/2014 | Higgins | G16B 40/00 |
| | | | 705/3 |
| 2014/0199698 A1 | 7/2014 | Rogan et al. | |
| 2014/0280327 A1 | 9/2014 | Pham et al. | |
| 2014/0359422 A1* | 12/2014 | Bassett, Jr. | G16C 20/30 |
| | | | 715/230 |
| 2015/0066378 A1 | 3/2015 | Robison et al. | |
| 2015/0100530 A1 | 4/2015 | Mnih et al. | |
| 2015/0142807 A1* | 5/2015 | Hofmann | G06F 16/245 |
| | | | 707/737 |
| 2015/0235143 A1* | 8/2015 | Eder | G16H 50/50 |
| | | | 706/12 |
| 2016/0314245 A1* | 10/2016 | Silver | G06N 7/005 |
| 2016/0364522 A1 | 12/2016 | Frey et al. | |
| 2017/0024642 A1 | 1/2017 | Xiong et al. | |
| 2017/0213127 A1* | 7/2017 | Duncan | G16B 50/00 |
| 2018/0107927 A1 | 4/2018 | Frey | |
| 2019/0252041 A1 | 8/2019 | Frey et al. | |
| 2019/0259473 A1* | 8/2019 | Och | G16B 20/20 |
| 2020/0097835 A1* | 3/2020 | Silver | G16H 50/70 |

FOREIGN PATENT DOCUMENTS

| | | |
|---|---|---|
| WO | WO-2012155148 A2 | 11/2012 |
| WO | WO-2013070634 A1 | 5/2013 |
| WO | WO-2016145516 A1 | 9/2016 |
| WO | WO-2016201564 A1 | 12/2016 |
| WO | WO-2017190211 A1 | 11/2017 |
| WO | WO-2017193198 A | 11/2017 |

OTHER PUBLICATIONS

Lundegaard et al. Prediction of epitopes using neural network based methods. (2011) J Immunological methods. vol. 374, pp. 26-34. (Year: 2011).*

Qang et al. DanQ: a hybrid convolutional and recurrent deep neural network for quantifying the function of DNA sequences. (Apr. 15, 2016) Nucleic Acids Research vol. 44, No. 11, e107. (Year: 2016).*

Weissbrod et al. Multikernel linear mixed models for complex phenotype prediction. (Jun. 14, 2016) Genome Research, vol. 26, pp. 969-979. (Year: 2016).*

González-Recio, O. et al. Machine learning methods and predictive ability metrics for genome wide prediction of complex traits. 2014 Livestock Science, vol. 166, pp. 217-219, plus supplemental information. (Year: 2014).*

Johansen, M, B. et al. Prediction of disease causing non-synonymous SNPs by the artificial neural network predictor NetDiseasesSNP. 2013 PLOS One, vol. 8 issue 7 e68730 and supplemental information. (Year: 2013).*

Kelley, D. R. et al. Basset: learning the regulatory code of the accessible genome with deep convolutional neural networks. (May 3, 2016) Genome Research, vol. 26 No. 7 pp. 990-999 and some supplemental material. (Year: 2016).*

Cerri et al. Hierarchical multi label classification using local neural networks. (2014) Journal of Computer and System Sciences, vol. 80, pp. 39-56. (Year: 2014).*

Zhou et al. Predicting effects of noncoding variants with deep learning based sequence model. (2015) Nature Methods vol. 12, No. 10, p. 931-939. (Year: 2015).*

Barash, et al. Deciphering the splicing code. Nature. May 6, 2010; 465 (7294):53-9. doi:10.1038/nature09000.

Co-pending U.S. Appl. No. 15/841,094, filed Dec. 13, 2017.

Hatzigeorgiou, et al. Functional site prediction on the DNA sequence by artificial neural networks. IEEE International Joint Symposia on Intelligence and Systems, Nov. 4-5, 1996, p. 12-17, Print ISBN: 0-8186-7728-7.

Hebsgaard, et al. Splice site prediction in *Arabidopsis thaliana* pre-mRNA by combining local and global sequence information. Nucleic Acids Res. Sep. 1, 1996; 24(17):3439-52.

(56) References Cited

OTHER PUBLICATIONS

Hinton, et al. Distilling the knowledge in a neural network. arXiv preprint arXiv:1503.02531 (2015).

Hinton, et al. Improving neural networks by preventing co-adaptation of feature detectors. arXiv preprint arXiv:1207.0580 (2012).

International Search Report corresponding to PCT/CA2016/050689; Canadian Intellectual Property Office; dated Jul. 27, 2016.

International search report dated Mar. 6, 2017 for PCT Application No. PCT/CA2016/050776.

International search report dated Dec. 22, 2016 for PCT Application No. PCT/CA2016/050510.

International Search Report for PCT/CA2016/050273, dated Jun. 15, 2016.

Leung, et al. Deep learning of the tissue-regulated splicing code. Bioinformatics vol. 30, pp. i121-i129, Jun. 15, 2014.

Office action dated Jul. 10, 2017 for U.S. Appl. No. 14/739,432.

Quang, et al. DANN: A deep learning approach for annotating the pathogenicity of genetic variants. Bioinformatics. Mar. 1, 2015; 31(5):761-3. doi: 10.1093/bioinformatics/btu703. Epub Oct. 22, 2014.

Reese, M. G. Application of a time-delay neural network to promoter annotation in the *Drosophila melanogaster* genome. Comput Chem. Dec. 2001; 26(1):51-6.

Srivastava, et al. Dropout: a simple way to prevent neural networks from overfilling. Journal of Machine _earning Research 15.1 (2014): 1929-1958.

Written Opinion of the International Search Authority for PCT/CA2016/050273, dated Jun. 15, 2016.

Written Opinion of the International Searching Authority corresponding to PCT/CA2016/050689; Canadian Intellectual Property Office; dated Jul. 27, 2016.

Xiong, et al. The human splicing code reveals new insights into the genetic determinants of disease. Science DOI: 10.1126/ science. 1254806. Published Online Dec. 18, 2014.

EP16810668 Extended European Search Report dated Jan. 15, 2019.

U.S. Appl. No. 14/739,432 Notice of Allowance dated Sep. 20, 2018.

U.S. Appl. No. 14/739,432 Office Action dated Jun. 1, 2018.

Manchon U, Eric Talevich, Samiksha Katiyar, Khaled Rasheed, & Natarajan Kannan. Prediction and Prioritization of Rare Oncogenic Mutations in the Cancer Kinome Using Novel Features and Multiple Classifiers. Apr. 2014. Computational Biology (Year : 2014).

U.S. Appl. No. 15/841,094 Office Action dated Jan. 11, 2021.

\* cited by examiner

NEURAL NETWORK ARCHITECTURES FOR LINKING BIOLOGICAL SEQUENCE VARIANTS BASED ON MOLECULAR PHENOTYPE, AND SYSTEMS AND METHODS THEREFOR

CROSS-REFERENCE

This application is a continuation application of PCT International Application No. PCT/CA2016/050689, filed Jun. 15, 2016, which is a continuation-in-part application of U.S. application Ser. No. 14/739,432, filed Jun. 15, 2015 (now U.S. Pat. No. 10,185,803, issued Jan. 22, 2019), each of which is incorporated herein by reference in its entirety.

TECHNICAL FIELD

The following relates generally to the field of genetic variant analysis and the field of neural network architectures, and more particularly to interpreting genetic variants to provide molecular phenotype information in support of precision medicine, genetic testing, therapeutic development, drug target identification, patient stratification, health risk assessment and connecting patients with rare disorders.

BACKGROUND

Precision medicine, genetic testing, therapeutic development, drug target identification, patient stratification, health risk assessment and connecting patients with rare disorders can benefit from accurate information about how biological sequence variants are different or are similar in their molecular phenotypes.

Biological sequence variants, also called variants, impact function by altering molecular phenotypes, which are aspects of biological molecules that participate in biochemical processes and in the development and maintenance of human cells, tissues, and organs.

In the context of medicine and the identification and understanding of genetic variants that cause disease, exonic variants that change amino acids or introduce stop codons have traditionally been the primary focus. Yet, since variants may act by altering regulatory processes and changing a variety of molecular phenotypes, techniques that focus on relating genetic variants to changes in molecular phenotypes are valuable. Over the past decade, this has led to molecular phenotype-centric approaches that go beyond traditional exon-centric approaches. This change in approach is underscored by several observations: while evolution is estimated to preserve at least 5.5% of the human genome, only 1% accounts for exons; biological complexity often cannot be accounted for by the number of genes (e.g. balsam poplar trees have twice as many genes as humans); differences between organisms cannot be accounted for by differences between their genes (e.g. less than 1% of human genes are distinct from those of mice and dogs); increasingly, disease-causing variants have been found outside of exons.

Analyzing how variants impact molecular phenotypes is challenging. In traditional molecular diagnostics, an example workflow may be as follows: a blood or tissue sample is obtained from a patient; variants (mutations) are identified, such as by sequencing the genome, sequencing the exome; running a gene panel; or applying a microarray; the variants are manually examined for their potential impact on molecular phenotype (e.g. by a technician), using literature databases and internet search engines; and a diagnostic report is prepared. Manually examining the variants is costly and prone to human error, which may lead to incorrect diagnosis and potential patient morbidity. Similar issues arise in therapeutic design, where there is uncertainty about the potential targets and their molecular phenotype mechanisms. Insurance increasingly relies on variant interpretation to identify disease markers and drug efficacy. Since the number of possible variants is extremely large, evaluating them manually is time-consuming, highly dependent on previous literature, and involves experimental data that has poor coverage and therefore can lead to high false negative rates, or "variants of uncertain significance". Automating or semi-automating the analysis of variants and their impact on molecular phenotypes is thus beneficial.

SUMMARY

In one aspect, a system for linking two or more biologically related variants derived from biological sequences is provided, the system comprising: one or more molecular phenotype neural networks (MPNNs), each MPNN comprising: an input layer configured to obtain one or more values digitally representing a variant in the two or more biologically related variants; one or more feature detectors, each configured to obtain input from at least one of: (i) one or more of the values in the input layer and (ii) an output of a previous feature detector; and an output layer comprising values representing a molecular phenotype for the variant, comprising one or more numerical elements obtained from one or more of the feature detectors; and a comparator linked to the output layer of each of the one or more MPNNs, the comparator configured to compare the molecular phenotypes for pairs of variants in the biologically related variants to determine a numerical link distance for the pairs of variants.

In another aspect, a method for linking two or more biologically related variants derived from biological sequences is provided, the method comprising: obtaining at an input layer of a molecular phenotype neural network (MPNN), two or more digital representations of the two or more biologically related variants, each comprising one or more input values; processing each variant by the MPNN, the MPNN comprising one or more feature detectors configured to obtain input from at least one of: (i) the one or more of the input values of the respective variant and (ii) an output of a previous feature detector, the MPNN configured to provide output values representing a molecular phenotype for the variant, comprising one or more numerical elements obtained from one or more of the feature detectors; for each of one or more pairs of variants in the two or more biologically related variants, determining, by a comparator, a numerical link distance, the determining comprising comparing the molecular phenotypes for the pair of variants.

The system may further comprise an encoder configured to generate the digital representation of the variant, the input layer being linked to an output of the encoder.

The encoder may further be configured to generate an encoded representation of one or more contexts, wherein the input layer is configured to obtain one or more values from the encoded representation of the one or more contexts.

The input layer may additionally be configured to obtain an additional one or more values digitally representing one or more contexts, wherein the molecular phenotype further comprises one or more numerical elements for each of one or more of the one or more contexts.

For a pair of variants processed by the MPNN, the comparator may determine the numerical link distance, by, for at least one of the one or more numerical elements in the molecular phenotype, applying one of the following linear or nonlinear functions to the difference between the molecular phenotype for a first variant in the pair of variants and the molecular phenotype for a second variant in the pair of variants: the identity operation, the square operation, and the absolute operation.

At least one of the variants in the two or more biologically related variants may be obtained from: a DNA, an RNA or a protein sequence of a patient; a sequence that would result when a DNA or an RNA editing system is applied, or a protein modification system is applied; a sequence where nucleotides targeted by a therapy are set to fixed values; a sequence where nucleotides targeted by a therapy are set to values other than existing values; and a sequence where nucleotides that overlap, fully or partially, with nucleotides that are targeted by a therapy are deactivated.

The molecular phenotype may comprise one or more of the following elements: percentage of transcripts that include an exon; percentage of transcripts that use an alternative splice site; percentage of transcripts that use an alternative polyadenylation site; the affinity of an RNA-protein interaction; the affinity of a DNA-protein interaction; the specificity of a microRNA-RNA interaction; the level of protein phosphorylation.

One or more variants in the two or more biologically related variants may be labeled variants, wherein labeled variants have associated labels, and the system may further comprise a labeling unit configured to associate labels with other variants comprising at least one variant in the two or more biologically related variants that are not labeled variants.

The labeling unit may further be configured to associate each other variant with the label of the variant in the labeled variants that has the lowest link distance to the respective other variant.

The number of other variants may be at least two, the labels may be comprised of one or more numerical values, and the two or more other variants may be sorted or partially sorted using one of the one or more numerical values in the labels.

For each other variant in the other variants, the MPNN may be configured to, for each labeled variant in the labeled variants, determine a numerical weight for the other variant and the labeled variant by applying a linear or a nonlinear weighting module to the link distance for a pair of variants consisting of the other variant and the labeled variant, and the labeling unit may be configured to, for each other variant of the other variants, determine an associated label by summing terms corresponding to the labeled variants, wherein each term is obtained by multiplying the numerical weight for the other variant and the corresponding labeled variant into the label associated with the corresponding labeled variant.

The MPNN may further be configured to, for each other variant in the other variants and for each labeled variant in the labeled variants, divide the numerical weight for the other variant and the labeled variant by the sum of the weights for the other variant and the labeled variants.

The number of other variants may be at least two and the labels may be comprised of one or more numerical values, and the system may be configured to sort or partially sort the two or more other variants using one of the one or more numerical values in the labels associated with the two or more other variants.

The system may further be configured to, for each of one or more pairs of variants in the two or more biologically related variants, obtain a measure of proximity of the pair of variants within the biological sequence, wherein the determining a numerical link distance further comprises combining the measure of proximity of the pair of variants with the comparing of the molecular phenotypes for the pair of variants.

The linear or the nonlinear weighting module may determine weights differently for different values of the labels.

Comparing the molecular phenotypes for the pairs of variants may comprise obtaining a link neural network, wherein the input of the link neural network comprises the molecular phenotypes for each pair of variants and wherein the output of the link neural network is the link distance for the pair of variants; and applying the link neural network to the molecular phenotypes for the pairs of variants.

The system may further be configured to obtain additional information pertaining to the similarity of function of the pair of variants, wherein the input of the link neural network further comprises the additional information.

The parameters of the link neural network may be determined using a training procedure applied to a dataset of examples, wherein each example comprises a pair of variants and a target value for the link distance.

These and other aspects are contemplated and described herein. It will be appreciated that the foregoing summary sets out representative aspects of methods and systems for producing an expanded training set for machine learning using biological sequences to assist skilled readers in understanding the following detailed description.

DESCRIPTION OF THE DRAWINGS

The features of the invention will become more apparent in the following detailed description in which reference is made to the appended drawings wherein.

DETAILED DESCRIPTION

Figure 1A:
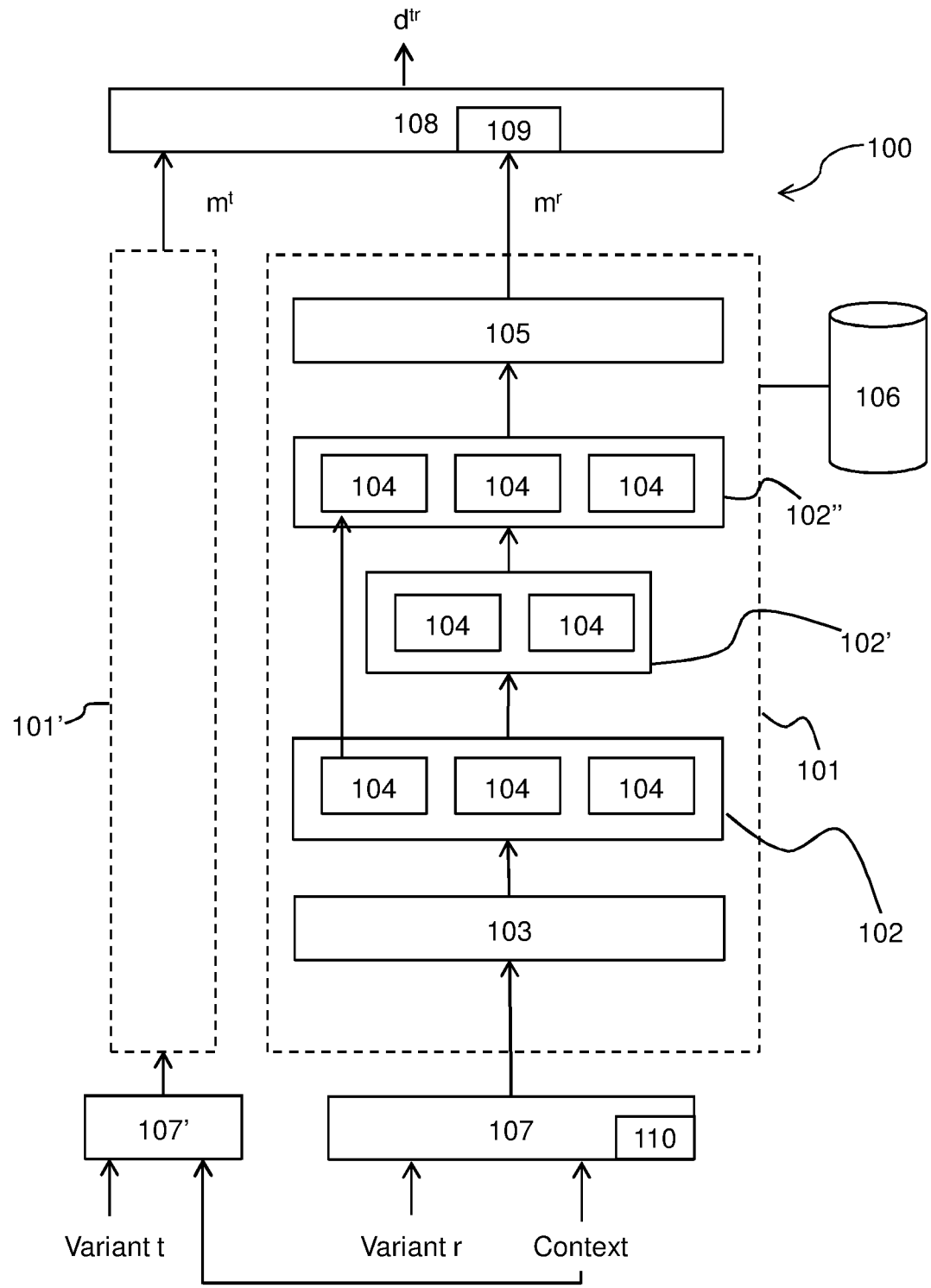
FIG. 1A is a block diagram illustrating a first embodiment of a system for linking biological sequence variants.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

A key unmet need in precision medicine is the ability to automatically or semi-automatically analyze biological sequence variants by examining their impact on molecular phenotypes.

The following provides systems and methods for determining links between biological sequence variants, also called variants, to other variants and generating scores for the strengths of the link between two variants according to the similarity in their molecular phenotypes. The systems generally comprise neural network architectures that are referred to herein as "molecular phenotype neural networks". The biological sequence may be a DNA sequence, an RNA sequence, or a protein sequence. Linked variants may be used in precision medicine to ascertain pathogenicity in genetic testing, to identify drug targets, to identify patients that respond similarly to a drug, to ascertain health risks, and to connect patients that have similar molecular phenotypes.

A biological sequence variant, also called a variant, is a biological sequence, such as a DNA sequence, an RNA sequence or a protein sequence, that may be derived from an existing biological sequence through a combination of substitutions, insertions and deletions. For example, the gene BRCA1 is represented as a specific DNA sequence of length 81,189 in the reference genome. If the samples from multiple patients are sequenced, then multiple different versions of the DNA sequence for BRCA1 may be obtained. These sequences, together with the sequence from the reference genome, form a set of variants.

To distinguish variants that are derived from the same biological sequence from those that are derived from different biological sequences, the following will refer to variants that are derived from the same biological sequence as "biologically related variants" and the term "biologically related" is used as an adjective to imply that a variant is among a set of biologically related variants. For example, the variants derived from the gene BRCA1 are biologically related variants. The variants derived from another gene, SMN1, are also biologically related variants. However, the variants derived from BRCA1 are not biologically related to the variants derived from SMN1. The term "biologically related variants" is used to organize variants according to their function, but it will be appreciated that this organization may be different according to different functions. For example, when they are transcribed, two different but homologous genes may generate the same RNA sequence. Variants in the RNA sequence may impact function in the same way, such as by impacting RNA stability. This is the case even though they originated from two different, albeit homologous, DNA sequences. The RNA sequence variants, regardless of from which gene they came, may be considered to be biologically related.

Biologically related variants may be derived naturally by DNA replication error; by spontaneous mutagenesis; by sexual reproduction; by evolution; by DNA, RNA and protein editing/modification processes; by retroviral activity, and by other means. Biologically related variants may be derived experimentally by plasmid construction, by gene editing systems such as CRISPR/Cas9, by sequencing samples from patients and aligning them to a reference sequence, and by other means. Biologically related variants may be derived computationally by applying a series of random or preselected substitutions, insertions and deletions to a reference sequence, by using a model of mutation to generate variants, and by other means. Biologically related variants may be derived from a DNA or RNA sequence of a patient, a sequence that would result when a DNA or RNA editing system is applied, a sequence where nucleotides targeted by a therapy are set to fixed values, a sequence where nucleotides targeted by a therapy are set to values other than existing values, or a sequence where nucleotides that overlap, fully or partially, with nucleotides that are targeted by a therapy are deactivated. It will be appreciated that there are other ways in which biologically related variants may be produced.

Depending on the function being studied, different sets of biologically related variants may be obtained from the same biological sequences. In the above example, DNA sequences for the BRCA1 gene of length 81,189 may be obtained from the reference genome and a group of patients and form a set of biologically related variants. As an example, if we are interested in how variants impact splicing of exon 6 in BRCA1, for each patient and the reference genome, we may extract a subsequence of length 600 nucleotides centered at the 3 prime end of exon 6. These splice site region sequences would form a different set of biologically related variants than the set of whole-gene biologically related variants.

The above discussion underscores that the functional meaning of a variant is context dependent, that is, dependent on the conditions. Consider the reference genome and an intronic single nucleotide substitution located 100 nucleotides from the 3 prime splice site of exon 6 in the BRCA1 gene. We can view this as two BRCA1 variants of length 81,189 nucleotides, or as two exon 6 splice site region variants of length 600 nucleotides, or, in the extreme, as two chromosome 17 variants of length 83 million nucleotides (BRCA1 is located on chromosome 17). Viewing the single nucleotide substitution in these three different situations would be important for understanding its impact on BRCA1 gene expression, BRCA1 exon 6 splicing, and chromatin interactions in chromosome 17. Furthermore, consider the same single nucleotide substitution in two different patients. Because the neighbouring sequence may be different in the two patients, the variants may be different.

A variant impacts function by altering one or more molecular phenotypes, which quantify aspects of biological molecules that participate in the biochemical processes that are responsible for the development and maintenance of human cells, tissues, and organs. A molecular phenotype may be a quantity, level, potential, process outcome, or qualitative description. The term "molecular phenotype" may be used interchangeably with the term "cell variable". Examples of molecular phenotypes include the concentration of BRCA1 transcripts in a population of cells; the percentage of BRCA1 transcripts that include exon 6; chromatin contact points in chromosome 17; the strength of binding between a DNA sequence and a protein; the strength of interaction between two proteins; DNA methylation patterns; RNA folding interactions; and inter-cell signalling. A molecular phenotype can be quantified in a variety of ways, such as by using a categorical variable, a single numerical value, a vector of real-valued numbers, or a probability distribution.

A variant that alters a molecular phenotype is more likely to alter a gross phenotype, such as disease or aging, than a variant that does not alter any molecular phenotype. This is because variants generally impact gross phenotypes by altering the biochemical processes that rely on DNA, RNA and protein sequences.

Since variants impact function by altering molecular phenotypes, a set of biologically related variants can be associated with a set of molecular phenotypes. BRCA1 whole-gene variants may be associated with the molecular phenotype measuring BRCA1 transcript concentration. BRCA1 exon 6 splice site region variants may be associated with the molecular phenotype measuring the percentage of BRCA1 transcripts that include exon 6. Chromosome 17 variants may be associated with the molecular phenotype measuring chromatin contact points in chromosome 17. This association may be one to one, one to many, many to one, or many to many. For instance, BRCA1 whole-gene variants, BRCA1 exon 6 splice region variants and chromosome 17 variants may be associated with the molecular phenotype measuring BRCA1 transcript concentration.

The association of a variant with a molecular phenotype does not imply for certain that the variant alters the molecular phenotype, it only implies that it may alter the molecular phenotype. An intronic single nucleotide substitution located 100 nucleotides from the 3 prime splice site of exon 6 in the BRCA1 gene may alter the percentage of BRCA1 transcripts that include exon 6, whereas a single nucleotide substitution located 99 nucleotides from the 3 prime splice site of exon 6 in the BRCA1 gene may not. Also, for the former case, whereas a G to T substitution may alter the molecular phenotype, a G to A substitution may not. Furthermore, the molecular phenotype may be altered in one cell type, but not in another, even if the variant is exactly the same. This is another example of context dependence.

The systems and methods described herein can be used to compare biologically related variants to one another by examining how they alter one or more associated molecular phenotypes. For example, the variants consisting of 600 nucleotides centered at the 3 prime end of exon 6 of BRCA1 obtained from a set of patients can be compared by examining how they alter the percentage of BRCA1 transcripts that include exon 6. If two variants cause the percentage of BRCA1 transcripts that include exon 6 to change in a similar way, the variants are more likely to be functionally related than if they cause the percentage of BRCA1 transcripts that include exon 6 to change in a different way.

There are different approaches to determining how variants alter the same molecular phenotype, ranging from experimental, to computational, to hybrid approaches.

The present systems comprise structured computational architectures referred to herein as molecular phenotype neural networks (MPNNs). MPNNs are artificial neural networks, also called neural networks, which are a powerful class of architectures for applying a series of computations to an input so as to determine an output. The input to the MPNN is used to determine the outputs of a set of feature detectors, which are then used to determine the outputs of other feature detectors, and so on, layer by layer, until the molecular phenotype output is determined. An MPNN architecture can be thought of as a configurable set of processors configured to perform a complex computation. The configuration is normally done in a phase called training, wherein the parameters of the MPNN are configured so as to maximize the computation's performance on determining molecular phenotypes or, equivalently, to minimize the errors made on that task. Because the MPNN gets better at a given task throughout training, the MPNN is said to be learning the task as training proceeds. MPNNs can be trained using machine learning methods. Once configured, an MPNN can be deployed for use in the task for which it was trained and herein for linking variants as described below.

Referring now to FIG. 1A, a system (100) comprises an MPNN (101) that is a neural network comprising a layer of input values that represents the variant (103) (which may be referred to as an "input layer"), one or more layers of feature detectors (102) and a layer of output values that represents the molecular phenotype (105) (which may be referred to as an "output layer"). Each layer of feature detectors (102, 102', 102") comprises one or more feature detectors (104), wherein each feature detector comprises or is implemented by a processor. Weights may be applied in each feature detector (104) in accordance with learned weighting, which is generally learned in a training stage of the neural network. The input values, the learned weights, the feature detector outputs and the output values may be stored in a memory (106) linked to the MPNN (101).

Figure 1B:
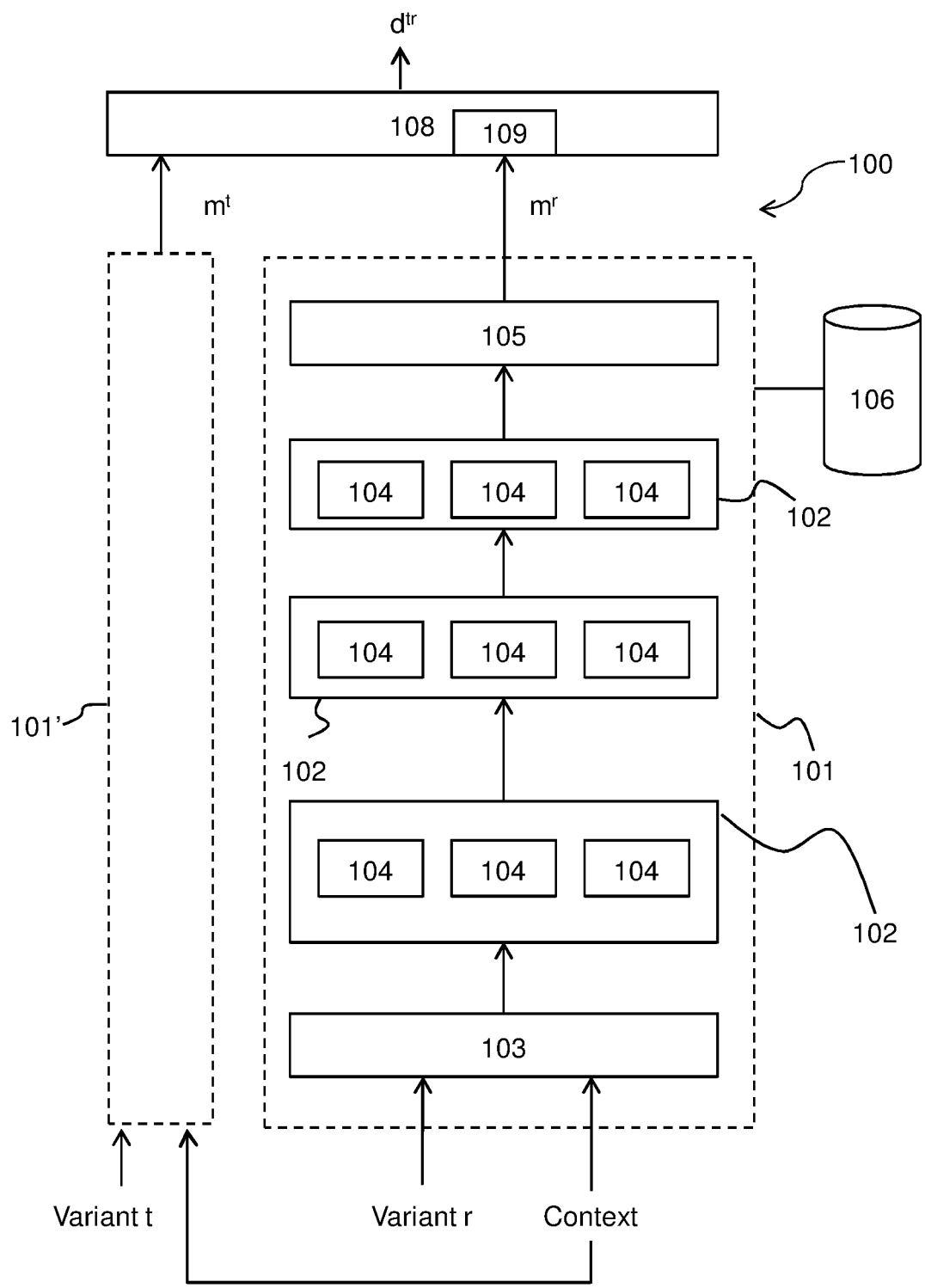
FIG. 1B is a block diagram illustrating a second embodiment of a system for linking biological sequence variants.
Figure 1C:
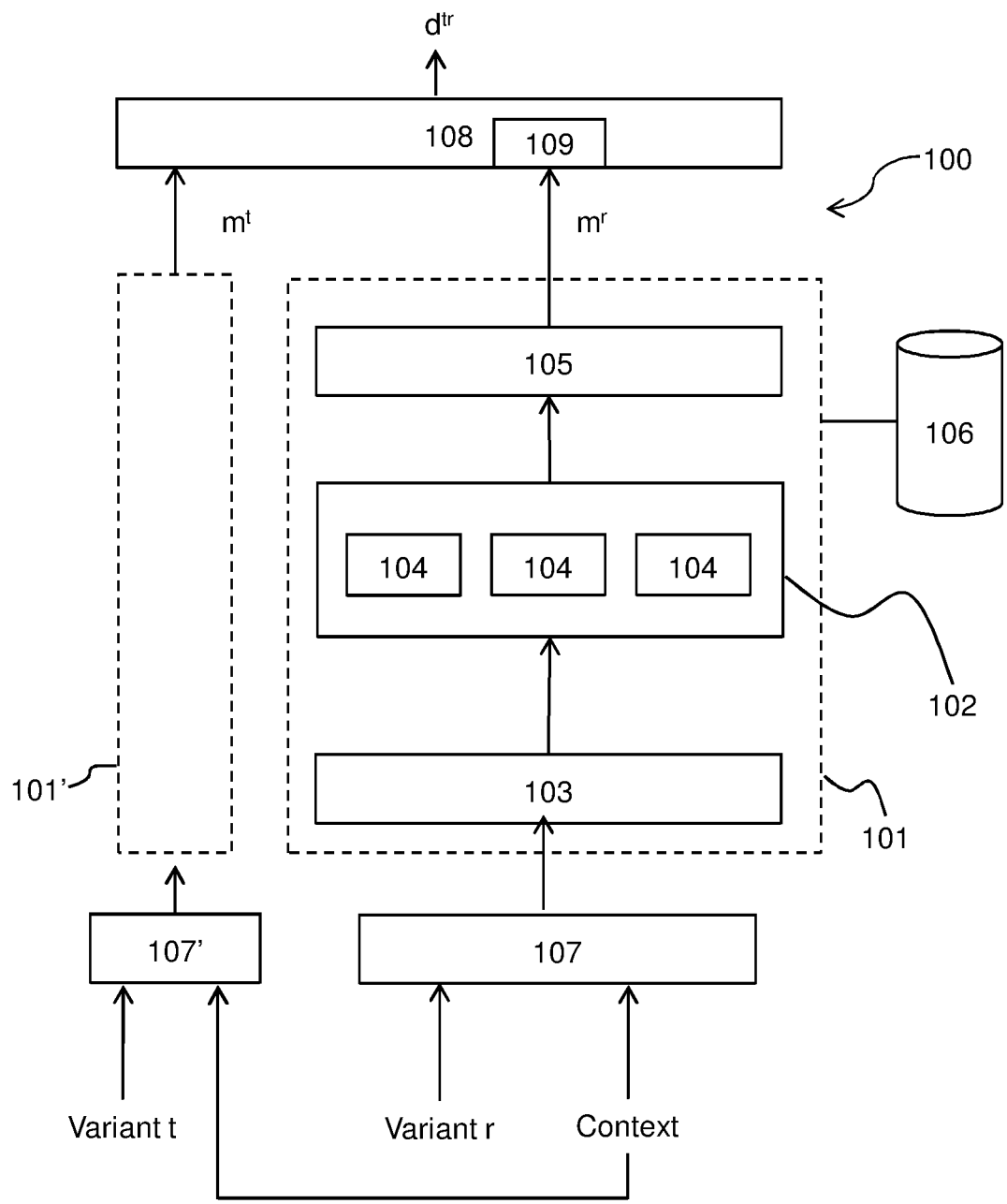
FIG. 1C is a block diagram illustrating a third embodiment of a system for linking biological sequence variants.
Figure 1D:
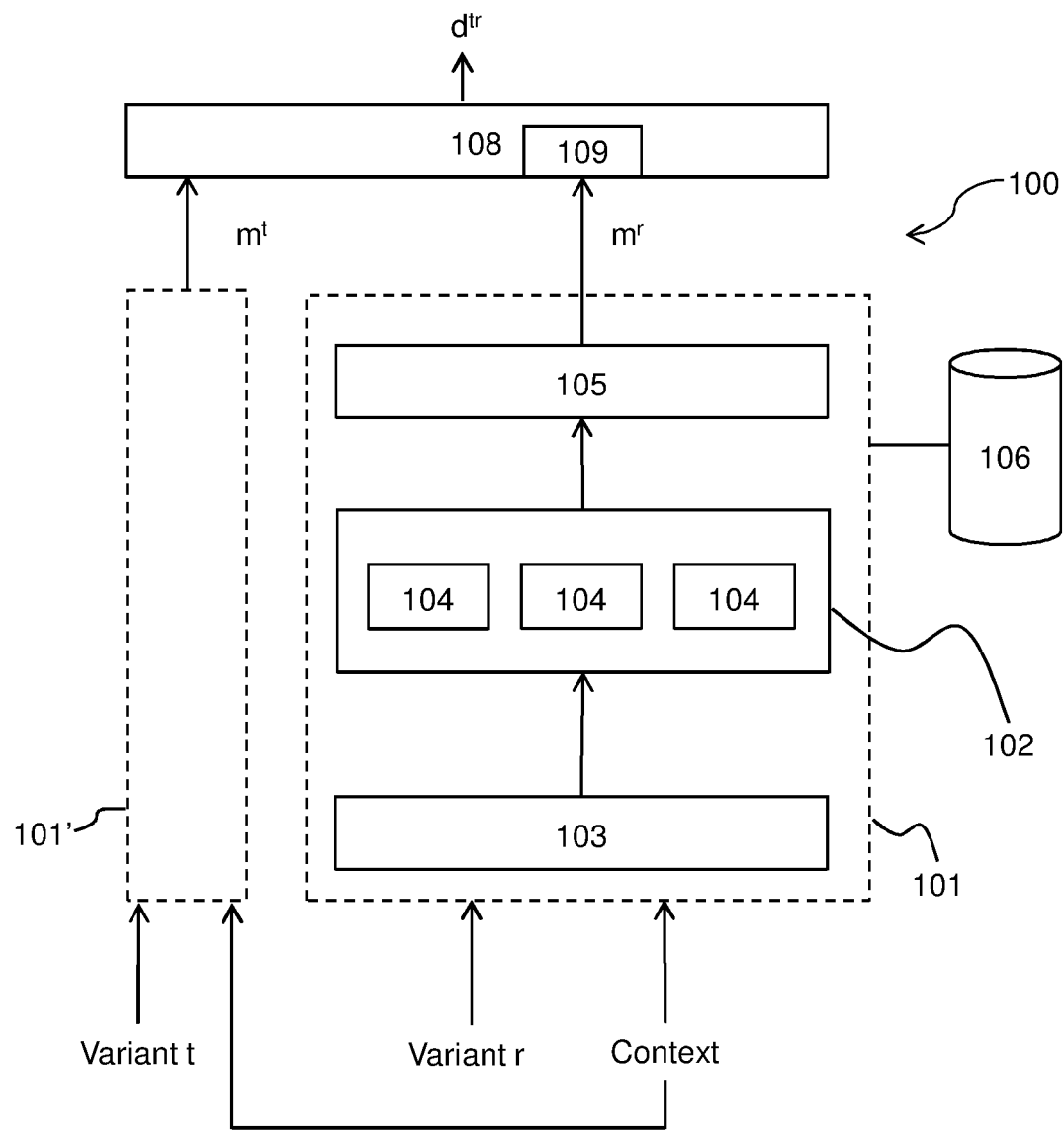
FIG. 1D is a block diagram illustrating a fourth embodiment of a system for linking biological sequence variants.

The particular MPNN (101) shown in FIG. 1A is an example architecture; the particular links between the feature detectors (104) may differ in various embodiments, which are not all depicted in the figures. A person of skill in the art would appreciate that such embodiments are contemplated herein. As an example, FIG. 1C and FIG. 1D show example MPNNs having one layer (102) of feature detectors (104).

Each layer (102, 102', 102") of feature detectors comprises the structured determination of the output of the feature detectors (104), and each feature detector (104) implements a computation that maps an input to an output. The feature detectors (104) in a layer accept a plurality of inputs from previous layers, combine them with a subset of weights, or parameters, W, and apply activation functions. Generally, the output of a feature detector in layer l may be provided as input to one or more feature detectors in layers l+1+1, l+2, . . . , L, where L is the number of layers of feature detectors. For example, in FIG. 1A, outputs of feature detectors (104) of layer (102) may be provided as input to one or more feature detectors (104) of a plurality of subsequent layers (102' and 102").

One or more feature detectors (104) may be implemented by processing hardware, such as a single or multi-core processor and/or graphics processing unit(s) (GPU(s)). Further, it will be understood that each feature detector (104) may be considered to be associated with an intermediate computation or an input of the neural network for an intermediate layer or an input layer, respectively. The use of large (many intermediate computations) and deep (multiple layers of computations) neural networks may improve the predictive performances of the MPNN compared to other systems.

As will be explained further, the systems and methods described herein use the MPNN to determine the molecular phenotypes of one or more pairs of biologically related variants, wherein the two variants in each pair will be referred to as variant t and variant r. The two corresponding molecular phenotypes are denoted $m^t$ and $m^r$ respectively. It may be advantageous for the system 100 to comprise a further MPNN (101'), wherein the further MPNN is identically trained and configured as the first MPNN (101). This may be the case, for example, where the cost of obtaining processors is low, the desire for increased speed is high and/or it is advantageous to perform variant analysis on the test variant and reference variant simultaneously. Alternatively, a single MPNN may be provided and the variants analysed one after the other, with the output of the first analysis being buffered at buffer (109) until the output of the second analysis is available.

The two molecular phenotypes $m^t$ and $m^r$ are analyzed using a comparator (108), which determines the link distance for the two variants, $d^{tr}$. It will be appreciated that when processing links between one variant and multiple other biologically related variants, the molecular phenotype of the one variant may be determined by one application of the MPNN, stored, and then fed into the comparator along with the molecular phenotype for every one of the multiple other biologically related variants. It will also be appreciated that when processing links between variants in a first set of variants and variants in a second set of variants, all of the molecular phenotypes of the variants in the first and second set of variants may be determined by applying the MPNN and then stored at buffer (109), and then the comparator may be applied to every pair of variants consisting of one variant from the first set of variants and one variant from the second set of variants.

Returning now to the MPNN (101 and 101'), MPNN can operate in two modes: the forward-propagation mode and the back-propagation mode. In the forward-propagation mode, the MPNN takes as input X, applies a series of computations resulting in intermediate values Z, and then applies computations to ascertain the output Y. The quantities X, Y and Z may each be a scalar value, a vector of values, or a set of values. The MPNN is configurable and its configuration is represented by parameters $W=(w_1, \ldots, w_p)$, where p is the number of parameters. For any choice of configuration W, we denote the output Y ascertained by the MPNN by $Y=F(X; W)$, where F defines the architecture of the MPNN.

Figure 1E:
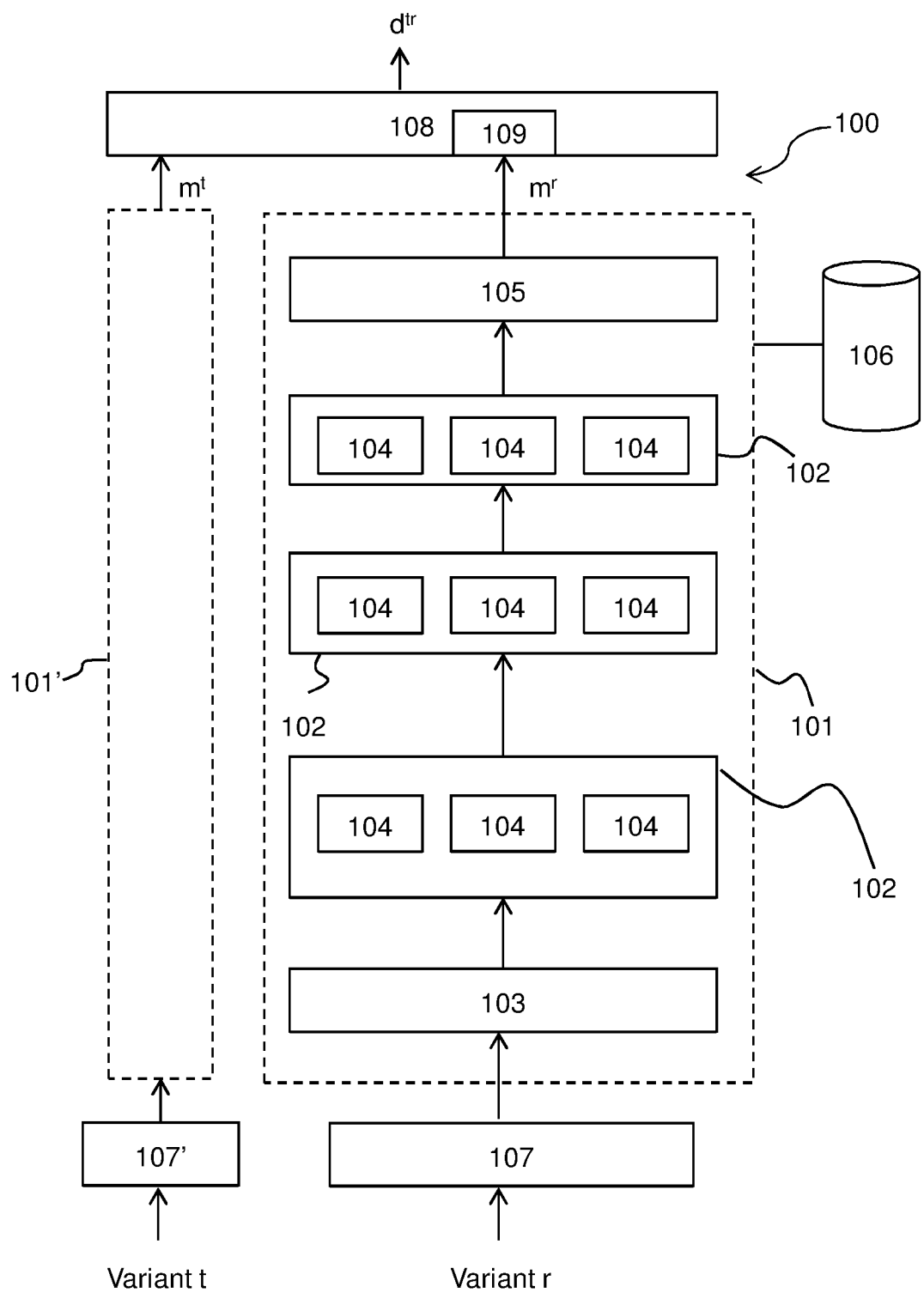
FIG. 1E is a block diagram illustrating a fifth embodiment of a system for linking biological sequence variants.

As shown in the system depicted in FIG. 1A, an MPNN takes as input a biological sequence and may also take as input a specification of the context. It then applies a structured series of computations, and outputs a numerical description of the molecular phenotype, which may comprise one or more numerical values or other information. The specification of the context may encode cell types, pairs of cell types, tissue types, age, sex, known biomarkers, patterns of behaviour, blood chemistry, and other environmental factors. It may also encode sequence context, such as the chromosome, gene or exon from which the input biological sequence was obtained. As shown in the system depicted in FIG. 1E, on the other hand, the MPNN may not take as input a context. The MPNN is configurable and its configuration is determined by a set of parameters using machine learning training. The MPNN can be applied to a set of biologically related variants to determine the corresponding variant molecular phenotypes.

MPNNs can be used to evaluate a variety of molecular phenotypes. In one example, an MPNN could take as input a sequence of 600 nucleotides centered at the 3 prime splice site of exon 6 in the BRCA1 gene and a specification of tissue type, and output the percentage of BRCA1 transcripts in that tissue type that include exon 6.

Examples of molecular phenotypes that may be predicted using MPNNs include exon inclusion levels/percentages, alternative splice site selection probabilities/percentages, alternative polyadenylation site selection probabilities/percentages for a transcript, affinity of an RNA-protein or DNA-protein interaction, RNA- or DNA-binding protein specificities, microRNA specificities, specificity of microRNA-RNA interaction, the level of protein phosphorylation, phosphorylation patterns, the distribution of proteins along a strand of DNA containing a gene, the number of copies of a gene (transcripts) in a cell, the distribution of proteins along the transcript, and the number of proteins.

The system (100) may further comprise an encoder (107) functionally coupled to the input layer of the MPNN so that biological sequences, which are discrete-symbol sequences, can be encoded numerically and used as inputs to the MPNN. The encoder may further encode the context to be input to the MPNN. It may be advantageous for the system 100 to comprise a further encoder (107'), wherein the further encoder is identical to the first encoder (107). This may be the case, for example, where the cost of obtaining processors is low, the desire for increased speed is high and/or it is advantageous to perform variant analysis on the test variant and reference variant simultaneously. Alternatively, a single encoder may be provided and the biological sequence and the context may be encoded one after the other, with the output of the first analysis being buffered at buffer (110) until the output of the second analysis is available. It will be appreciated that the encoder may be applied in different ways and that an encoder may not be used at all, as depicted in FIG. 1B and FIG. 1D.

The encoder may, for example, encode the sequence of symbols in a sequence of numerical vectors (a vector sequence) using one-hot encoding. Suppose the symbols in the sequence come from an alphabet $A=(\alpha_1, \ldots, \alpha_k)$ where there are k symbols. The symbol $s_i$ at position i in the sequence is encoded into a numerical vector $x_i$ of length k: $x_i=(x_{i,1}, \ldots, x_{i,k})$ where $x_{i,j}=[s_i=\alpha_j]$ and $[\cdot]$ is defined such that [True]=1 and [False]=0 (so called Iverson's notation). One-hot encoding of all of the biological sequence elements produces an m×r matrix X. For example, a DNA sequence CAAGTTT of length n=7 and with an alphabet A=(A, C, G, T), such that k=4, would produce the following vector sequence:

$$X = \begin{pmatrix} 0 & 1 & 1 & 0 & 0 & 0 & 0 \\ 1 & 0 & 0 & 0 & 0 & 0 & 0 \\ 0 & 0 & 0 & 1 & 0 & 0 & 0 \\ 0 & 0 & 0 & 0 & 1 & 1 & 1 \end{pmatrix}.$$

Such an encoding is useful for representing biological sequences as numeric inputs to the neural network. It will be appreciated that other encodings of X may be computed from linear or non-linear transformations of a one-hot encoding, so long as the transformed values are still distinct, or that other encodings may be used.

The MPNN also takes as input a specification of context, which may be numerical, categorical or an additional sequence. The specification of context may also in part be encoded by the encoder using, for example, a one-hot encoding scheme.

It is useful to compare the output of a MPNN Y to a desired output or target, Y'. The molecular phenotype target may be ascertained using experimental techniques, such as RNA-Seq, ChIP-Seq, microarrays, RT-PCR, SELEX, and massively parallel reporter assays. This is useful for training, in which the MPNN is configured using the parameters W such that, for input-target pairs (X, Y') in the training set of many such input-target pairs, the MPNN's output $Y=F(X; W)$ is a good approximation of the training target Y', across the input-output pairs in the training set. The error or cost between the MPNN output Y and a target Y' can be quantified by, for example, the squared error $(Y-Y')^2$. It will be appreciated that different error or cost functions may be used. The error term is incorporated into a loss function $L(X, Y'; W)$, which measures the discrepancy between the output of the MPNN and the desired output. In the example, $L(X, Y'; W)=(F(X; W)-Y')^2$. The process of training involves configuring W so as to minimize the total loss in a training set, such as the sum over the training examples of the loss for each example. Training may consist of determining a configuration W that minimizes or approximately minimizes the expected value or sum of L for pairs (X, Y') sampled from either training set or from a held-out validation set.

Alternatively or additionally, the MPNN may be operated in the back-propagation mode, which is used to determine how changes in the intermediate computations, the inputs, and the parameters will impact the output of the MPNN. These three types of changes are called gradients or derivatives and are denoted $\partial Y/\partial Z$, $\partial Y/\partial X$ and $\partial Y/\partial W$ respectively. Note that while Z is not explicit in the input-output relationship $Y=F(X; W)$, the output depends on the intermediate computations and so the gradient of the output with respect to the values produced by the intermediate computations can be determined. These gradients are useful for training.

An MPNN operating in back-propagation mode is a structured architecture that comprises a series of computations in a structured framework. First, the MPNN is operated in the forward-propagation mode to compute $Y=F(X; W)$. Then, the MPNN is operated in the back-propagation mode, which comprises a series of computations that starts with the output of the MPNN and works its way back to the input, so as to determine the gradients $\partial Y/\partial Z$, $\partial Y/\partial X$ and $\partial Y/\partial W$ for values produced by all of the intermediate computations Z, for all inputs X, and for all parameters W.

MPNNs are configured by training their parameters using one or more neural network training procedures applied to a training dataset. The dataset consists of examples of biological sequences, specifications of context, and corresponding molecular phenotypes. An important aspect of MPNNs is their ability to generalize to new conditions, that is, to biological sequences and contexts that are not in the training dataset. This aspect enables MPNNs to determine the molecular phenotypes of variants that are not in the training dataset or to variant-context combinations that are not in the training dataset.

In one example, an MPNN takes as input a subsequence of length 600 nucleotides centered at the 3 prime end of exon 6 in BRCA1 (a splice site region variant), and a one-hot encoding of the cell type, and through a structured series of computations determines the percentage of BRCA1 transcripts that include exon 6. This MPNN may have been trained using BRCA1 exon 6 splice region variants and corresponding measurements of splicing percentages, obtained by DNA and RNA sequencing of patients. This MPNN can be used to analyze BRCA1 exon 6 splice site region variants. It can also be used to analyze splice site region variants from other exons in BRCA1 and even for other exons in other genes, but it may not be accurate in these cases because it was trained using only data for exon 6 in BRCA1.

In another example, an MPNN takes as input a subsequence of length 600 nucleotides centered at the 3 prime end of any exon in the human genome, and a one-hot encoding of the cell type, and through a structured series of computations determines the percentage of transcripts that include the exon, out of all those transcripts generated from the gene containing the exon. This MPNN may have been trained using splice region variants from chromosomes 1 to 10 and corresponding measurements of splicing percentages, obtained by DNA and RNA sequencing of a single healthy individual. This MPNN can be used to analyze BRCA1 exon 6 splice site region variants, but it can also be used to analyze splice site region variants from other exons in BRCA1 and for other exons in other genes. Even though it was trained using data for chromosomes 1 to 10, it may generalize well to the other chromosomes.

In another example, an MPNN takes as input a subsequence of length 600 nucleotides centered at the 3 prime end of any exon in the human genome, and a one-hot encoding of the cell type, and a one-hot encoding of the gene in which the exon is located, and through a structured series of computations determines the percentage of transcripts that include the exon, out of all those transcripts generated from the gene containing the exon. By providing the gene identity as input to the MPNN, the MPNN may account for gene-specific effects on the molecular phenotype, as well as for gene-independent effects.

The MPNN examples described above may all be implemented by the same or possibly different MPNN structures; that is, the number, composition and parameters of the nodes and layers may or may not differ. It will be appreciated that the biological sequences need not be of the same length and that an MPNN may be trained to account for other molecular phenotypes, for other biologically related variants and for other specifications of context.

The MPNN may be configured in different ways such as to use a discriminative neural network, a convolutional neural network, an autoencoder, a multi-task neural network, a recurrent neural network, a long short-term memory neural network, or a combination thereof. It will also be appreciated that many different machine learning architectures can be represented as neural networks, including linear regression, logistic regression, softmax regression, decision trees, random forests, support vector machines and ensemble models. Differences between techniques and architectures often pertain to differences in the cost functions and optimization procedures used to configure the architecture using a training set.

It will also be appreciated that the MPNN may also take as input a vector of features that are derived from the variant sequence. Examples of features include locations of protein binding sites, RNA secondary structures, chromatin interactions, and protein structure information.

It will be appreciated that the MPNN may be applied to a set of variants to determine the molecular phenotypes of the variants in the set of variants.

Since biologically related variants may be derivable from a reference sequence, in another embodiment, the MPNN is used to determine the molecular phenotype of a variant as it relates to the molecular phenotype of the reference sequence. For example, consider an MPNN that is configured to determine the percentage of transcripts that include exon 6 of BRCA1 using the 600 nucleotide sequence centered at the 3 prime end of the exon. The MPNN may be applied to the reference sequence extracted from the reference genome, and also to the variants from the patient. The percentage value for the reference genome may be subtracted from the percentage values for the patients, resulting in variant molecular phenotypes that measure the change in the percentage. It will be appreciated that the comparison of the variant and the reference sequence may be performed in different ways, including using the difference, the absolute difference and the squared difference. For multi-valued molecular phenotypes, the sum of the differences, the sum of the absolute differences and the sum of the squared differences may be used. For probability distributions, Kullback-Leibler divergence may be used. For example, if the output of the MPNN is a probability distribution over a discrete variable, the variant molecular phenotype may be computed using the Kullback-Leibler divergence between the probability distribution ascertained from the variant and the reference sequence. It will be appreciated that more than one reference sequence may be used and the comparison may be adjusted accordingly, such as by determining the maximum or the average of the differences between the outputs for the variant and the references. It will be appreciated that the one or more reference sequences may be obtained in different ways, such as by sequencing the DNA from one or more close relatives of the patient; by examining the reference genome, the reference transcriptome or the reference proteome; by sequencing a gene using a sample from a patient's tumour; or by sequencing the gene using a sample from an unaffected tissue in the same patient.

Unlike many existing systems, the methods and systems described herein can be used to analyze variants in different contexts. For instance, when a child's variant is compared to a reference sequence obtained from the reference human genome, the MPNN may produce a large variant-induced molecular phenotype, indicating that the variant may be disease causing. But, when the same variant is compared to the reference sequences obtained from his or her unaffected parents, the MPNN may produce a low variant-induced molecular phenotype, indicating that the variant may not be disease causing. In contrast, if the MPNN produces a large variant-induced molecular phenotype when the parents' sequences are used as the reference, then the variant is more likely to be the cause of the disease.

Another circumstance in which different reference sequences arise is when the variant may be present in more than one transcript, requiring that the impact of the variant be ascertained in a transcript-dependent fashion. Also, since the MPNN takes as input a description of the environment, such as a one-hot encoding of the cell type, the variant-induced molecular phenotype can depend on the context as established by the environment. A variant may not induce a molecular phenotype in a liver cell, but induce a large molecular phenotype in a brain cell.

Figure 12:
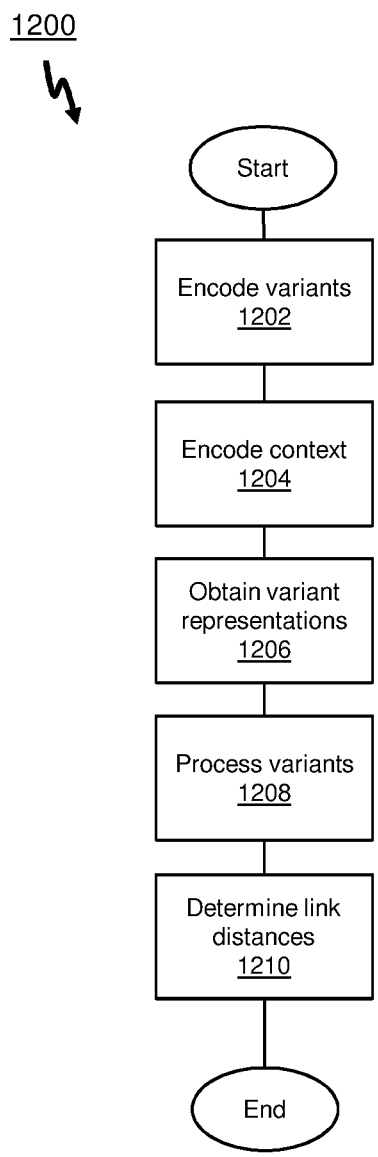
FIG. 12 is a flowchart showing a method for linking biological sequence variants.

FIG. 12 illustrates a flowchart that summarizes the above steps performed by system 100. A method (1200) for linking two or more biologically related variants derived from biological sequences comprises: at block 1202, each of two or more digital representations of the two or more biologically related variants may be generated by the encoder; at block 1204, digital representations of the one or more contexts may be generated by the encoder; at block 1206, obtaining at an input layer of a molecular phenotype neural network (MPNN), each of the two or more digital representations of the two or more biologically related variants, each comprising one or more input values digitally representing a variant and, possibly, the one or more contexts; at block 1208, processing each variant by the MPNN, the MPNN comprising one or more feature detectors configured to obtain input from at least one of: (i) the one or more of the input values of the respective variant and (ii) an output of a previous feature detector, the MPNN configured to provide output values representing a molecular phenotype for the variant, comprising one or more numerical elements of one or more of the feature detectors; at block 1210, for each of one or more pairs of variants in the two or more biologically related variants, determining, by a comparator, a numerical link distance comprising comparing the molecular phenotypes for the pair of variants.

Figure 2:
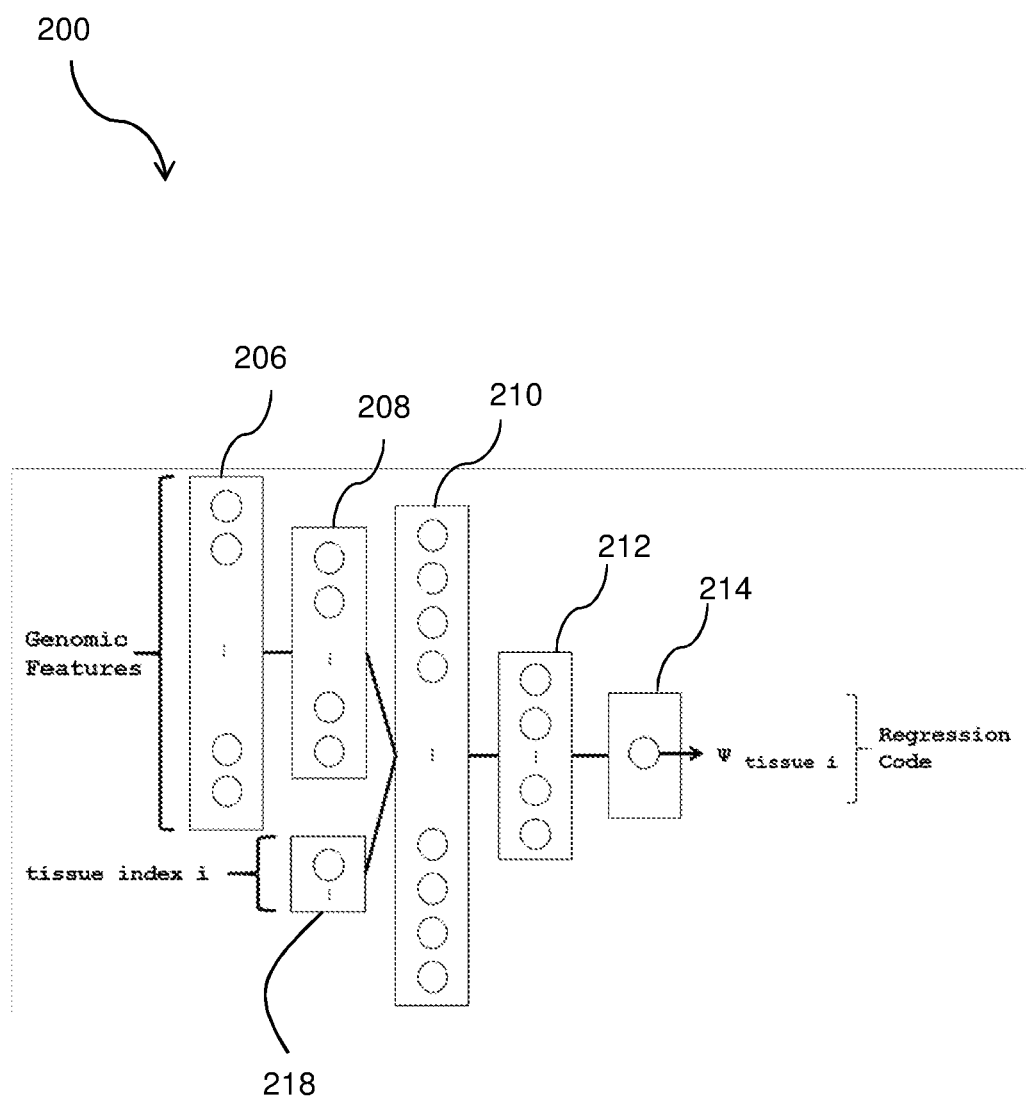
FIG. 2 is a block diagram illustrating a first example architecture of a molecular phenotype neural network.

Referring now to FIG. 2, shown therein is an example architecture (200) of an MPNN that has a layer of input values that represent genomic features (206) that are DNA sequences, encoded DNA sequences, or other features derived from DNA sequences, wherein the DNA sequences containing an exon, the neighbouring introns and the neighbouring exons as well as the annotated splice junctions. The layer of input values also includes a specification of the context in the form of the tissue index (218). In this example, where are three layers of feature detectors (208, 210 and 212). In this example, using these layers of feature detectors, the MPNN processes the inputs through three layers of feature detectors (208, 210, 212) that apply a structured series of computations to determine an output (214), which in this example is the percentage of transcripts that include the exon $\Psi$, at the output layer. This MPNN may be viewed as a regression model. The input values representing genomic features comprise input to the first layer of feature detectors (208). In this example, the input values representing the tissue index (218) and the outputs of the feature detector from the first layer of feature detectors (208) comprise the inputs to the second layer of feature detectors (210). The outputs of the second layer of feature detectors (210) comprise the inputs to the third and final layer of feature detectors (212). The outputs of the third and final layer of feature detectors (212) are the molecular phenotype values (214). It will be appreciated that different architectures may be used. For example, the input values representing the tissue index (218) may be inputs to the first layer of feature detectors (208) and the first layer of feature detectors may be the final layer of feature detectors and the outputs of the first layer of feature detectors may be the molecular phenotype values (214). For example, there may be more than three layers of feature detectors. The values in the input layer may be inputs to the second and third layers of feature detectors. It will be appreciated that values in the input layer may be derived in different ways or encoded in different ways. For example, the values in the input layer (206) may include binding specificities of RNA- and DNA-binding proteins, RNA secondary structures, nucleosome positions, position-specific frequencies of short nucleotide sequences, and many others. The context (e.g., tissue index) may also be derived or encoded in different ways, such as by using an encoder (not shown), which encodes the tissue index i using a 1-of-TT binary vector where TT represents the number of conditions and the values in the vector are zero everywhere except at the position indicating the condition, where the value is one. This is called one-hot encoding.

Figure 3:
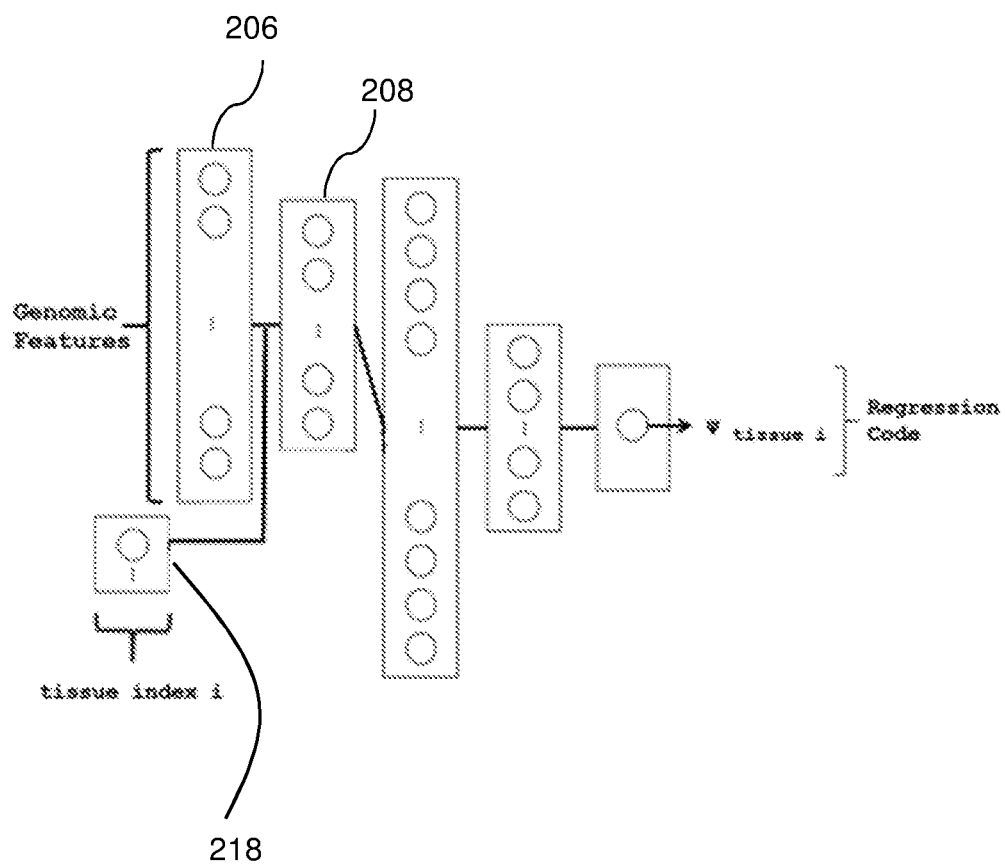
FIG. 3 is a block diagram illustrating a second example architecture of a molecular phenotype neural network.

FIG. 3 shows another example where the input values representing context (204) along with the input values representing genomic features comprise inputs to the first layer of feature detectors (208)

Figure 4:
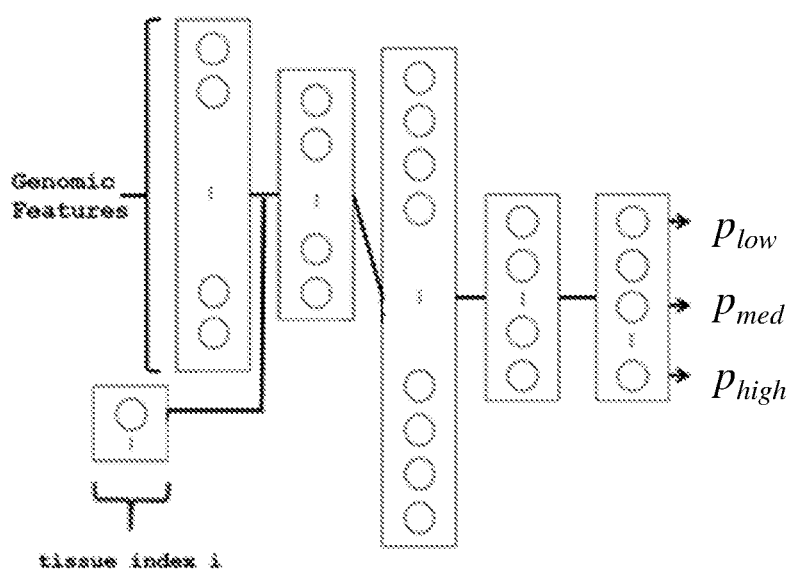
FIG. 4 is a block diagram illustrating a third example architecture of a molecular phenotype neural network.

Referring now to FIG. 4, it will be appreciated that the molecular phenotype may be represented in different ways. Instead of determining a real-valued $\Psi$ in the form of a percentage, the MPNN may output probabilities over discrete molecular phenotype categories. For example, the percentage may be binned into low (between 0 and 33%), medium (34% to 66%) and high (67% to 100%), and the output of the MPNN may be three real numbers between zero and one that add up to one: $p_{low}$, $p_{med}$, $p_{high}$. The molecular phenotype targets for training this MPNN may be one-hot encoded vectors, (1,0,0), (0,1,0) and (0,0,1), or probabilities distributions that take into account measurement noise. For these discretized molecular phenotype values, the cross entropy cost function or the log-likelihood performance measure can be used for training.

Figure 5:
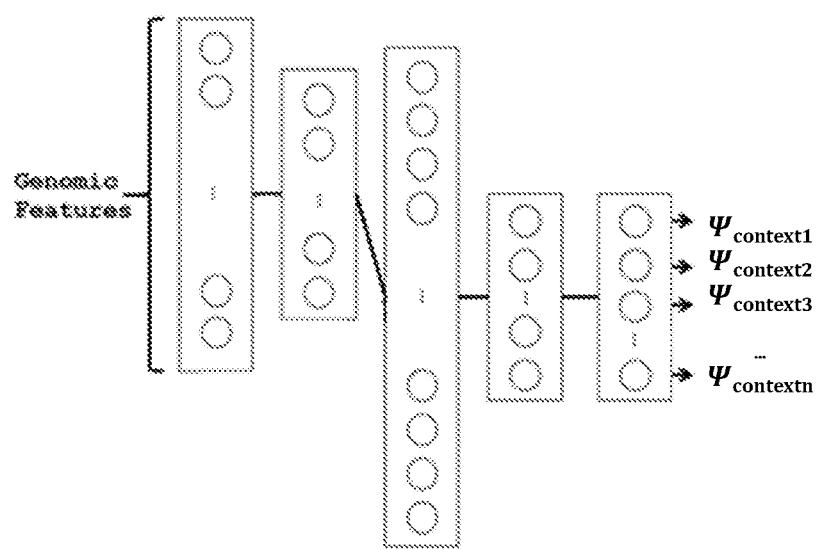
FIG. 5 is a block diagram illustrating a fourth example architecture of a molecular phenotype neural network.
Figure 6:
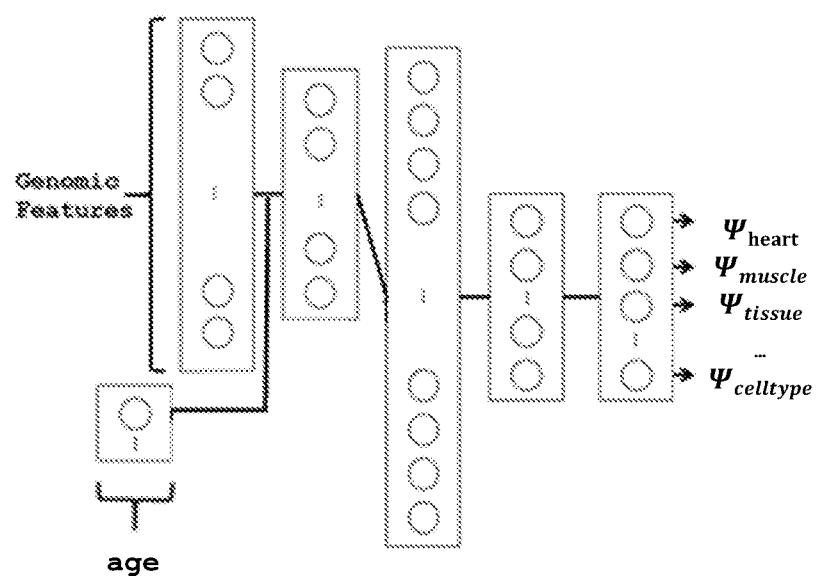
FIG. 6 is a block diagram illustrating a fifth example architecture of a molecular phenotype neural network.

Referring now to FIG. 5, it will be appreciated that instead of encoding the context as an input to the MPNN, the MPNN may output a different molecular phenotype value for each context. Here, the MPNN determines the percentage of transcripts that include the exon for every one of the T tissue types. These T numerical values together comprise the molecular phenotype. It will be appreciated that hybrid approaches are possible, where part of the context is provided as input and the molecular phenotype is provided for every other aspect of the context. Referring now to FIG. 6, for example, the age of the patient may be provided as an input to the MPNN, and the MPNN may provide a molecular phenotype value for each of T different tissue types, such as heart, muscle, tissue, etc.

Referring back to FIG. 1A, in the training phase, the MPNN (101) can be configured by adjusting its parameters using a dataset of biological sequences, specifications of context, and corresponding molecular phenotypes. This comprises establishing an MPNN and then repeatedly updating the one or more parameters, or weights, of the MPNN so as to decrease the error between the molecular phenotypes determined using the MPNN and the measured molecular phenotypes, until a condition for convergence is met at which point the parameters are no longer updated. It will be appreciated that instead of decreasing the error, the objective may be to decrease another loss function such as cross entropy, or to maximize an objective function, such as log-likelihood. The resulting parameters, or weights, are then stored in the memory (106) such that the MPNN parameters can be reused during application to analyze variants. At each step of the updating of one or more parameters, the entire batch of data may be used, or a subset of examples called a minibatch may be used, the examples in the minibatch being selected randomly or by using a predetermined pattern.

Referring again to FIG. 1A, embodiments comprising a comparator (108) can be used to link variants by using MPNNs to determine the variant molecular phenotypes and then, for any two variants, determining a link distance by comparing their molecular phenotypes. These link distances are used to identify, score, prioritize or rank the variants. Knowledge about one variant can be associated with another variant by examining the link distance. Knowledge may include English language descriptions, interpretations and mechanistic explanations; functional annotations; and literature references.

For two variants, the comparator may determine the link distance as a numerical value indicating the strength of the link between the two variants, where a strong link has a low link distance and a weak link has a high link distance. The link distances between a test variant and multiple established variants can further be compared to identify which established variants are most strongly linked to the test variant.

In conjunction with link distances, the term "prioritization" is used herein to refer to the process of producing a sorted list of variants to identify the order in which variants should be examined, processed, classified, or otherwise considered for further analysis.

In one embodiment, for one or more pairs of biologically related variants, the MPNN is used to determine the variant molecular phenotype for every variant. The comparator determines link distance between the variants in each pair by summing the output of a nonlinear function applied to the difference between the molecular phenotypes for the two variants. The nonlinear function may be the square operation. The nonlinear function may be the absolute operation.

In one embodiment, the link distance between a pair of variants t and r for context c is determined by first ascertaining their real-valued molecular phenotypes $m_c^t$ and $m_c^r$ using the MPNN. The context-specific link distance $d^{tr}$ between the two variants may be computed using one of the formulas:

$$d^{tr}=m_c^t-m_c^r, d^{tr}=(m_c^t-m_c^r)^2, d^{tr}=|m_c^t-m_c^r|,$$

where $|\cdot|$ is the absolute function. This may be repeated for all pairs of biologically related variants or for a subset of pairs. It will be appreciated that the MPNN need be applied only once for each variant, and that the comparator (108) may apply various other computations to compute the link distance.

In another embodiment, the molecular phenotype determined using the MPNN is a vector of values, so that $m_c^t=(m_{c,1}^t, m_{c,1}^t, \ldots, m_{c,q}^t)$ and $m_c^r=(m_{c,1}^r, m_{c,1}^r, \ldots, m_{c,q}^r)$. The context-specific link distance between the two variants may be computed using one of the operations:

$$d^{tr} \leftarrow \Sigma_{n=1}^{q}(m_{c,n}^t-m_{c,n}^r), d^{tr} \leftarrow \Sigma_{n=1}^{q}(m_{c,n}^t-m_{c,n}^r)^2,$$
$$d^{tr} \leftarrow \Sigma_{n=1}^{q}|m_{c,n}^t-m_{c,n}^r|,$$

where $|\cdot|$ is the absolute function. This may be repeated for all pairs of biologically related variants or for a subset of pairs. It will be appreciated that the MPNN need be applied only once for each variant, and that the comparator (108) may apply various other computations to compute the link distance.

In another embodiment, the molecular phenotype is a vector of values corresponding to probabilities over different possible categories, the probabilities summing to one. The context-specific link distance between the two variants may be computed using an operation that accounts for probabilities in the fashion of the Kullback-Leibler divergence:

$$d^{tr} \leftarrow \Sigma_{n=1}^q m_{c,n}{}^t \log(m_{c,n}{}^t/m_{c,n}{}^r), d^{tr} \leftarrow \Sigma_{n=1}^q m_{c,n}{}^r \log(m_{c,n}{}^r/m_{c,n}{}^t),$$

In another embodiment, the molecular phenotypes for every context c=1 ... T is determined using the MPNN and they are placed in a vector for each pair of variants: $m^t = (m_1{}^t, \ldots, m_T{}^t)$ and $m^r = (m_1{}^r, \ldots, m_T{}^r)$ wherein T is the number of contexts. The link distance between the two variants may be computed using one of the formulas:

$$d^{tr} \leftarrow \Sigma_{c=1}^T (m_c{}^t - m_c{}^r), d^{tr} \leftarrow \Sigma_{c=1}^T (m_c{}^t - m_c{}^r)^2,$$
$$d^{tr} \leftarrow \Sigma_{c=1}^T |m_c{}^t - m_c{}^r|.$$

When summing across contexts, predetermined numerical scaling factors may be used to give higher weight to some conditions compared to others. Denote the set of scale factors for the different conditions by $a_1, \ldots, a_T$. One of the following formulas may be used to compute the link distance:

$$d^{tr} \leftarrow \Sigma_{c=1}^T a_c(m_c{}^t - m_c{}^r), d^{tr} \leftarrow \Sigma_{c=1}^T a_c(m_c{}^t - m_c{}^r)^2,$$
$$d^{tr} \leftarrow \Sigma_{c=1}^T a_c|m_c{}^t - m_c{}^r|.$$

This may be repeated for all pairs of biologically related variants or for a subset of pairs. It will be appreciated that the MPNN need be applied only once for each variant. It will be appreciated that the comparator may apply various other computations to compute the link distance.

It will be appreciated that this method can be applied using MPNNs that compute several different molecular phenotypes and these may be combined to determine link distances. It will be appreciated that multiple MPNNs may be applied to compute multiple molecular phenotypes and these may be combined to determine link distances. It will be appreciated that multiple MPNNs may be applied to compute multiple link distances and that these may be combined to determine link distances.

Figure 11:
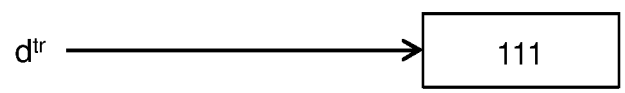
FIG. 11 is a block diagram showing a labeling unit.

In another aspect, for a set of biologically related variants wherein some of the variants are labeled, the MPNN-determined link distances between the other variants and the labeled variants can be used to associate the labels with the other variants. The label of one of the other variants may be determined by computing the link distances of the other variant to one or more of the labeled variants. The label of the other variant may be determined from the label of the labelled variant that has the lowest link distance. Alternatively, the label of the other variant may be determined by computing the weighted average of the labels of the labelled variants, where the weights are nonlinear functions of the link distances. Two or more other variants may be prioritized, by sorting them according to their label values. Two or more other variants may be partially sorted according to their label values, that is, the k other variants with smallest link distance may be identified and sorted, where k is smaller than the number of other variants. The determined label may be applied to the variant by the labeling unit (111), as shown in FIG. 11.

To illustrate, suppose the system determines that a test variant causes a change in a particular molecular phenotype, say the splicing level of a specific exon. Suppose a nearby, labelled variant whose disease function is well characterized causes a similar change in the exact same molecular phenotype. Since variants act by changing cellular chemistry, such as the splicing level of the exon, it can be inferred that the test variant likely has the same functional impact as the labelled variant. The system can ascertain the link distance between the two variants in this fashion using a variety of different measures. Because the MPNN can take a specification of context, such as cell type, as input, this information can be used to more accurately associate variants with one another. For example, two variants that have similar molecular phenotypes in brain tissue would be associated more strongly than two variants that have similar molecular phenotypes, but in different tissues.

One class of labels measure deleteriousness. A "deleteriousness label" is a classification, category, level or numerical value that is associated with a variant and that relates its level of deleteriousness for one or more functions or categories. It may be derived using evolutionary analysis, an analysis of how severely the variant damages a biological process or biomolecule, knowledge about the variant's disease function, or other information pertaining to the variant. A deleteriousness label may contain a set of numerical values that each indicates the degree of deleteriousness in one of multiple categories of deleteriousness. It will be appreciated that deleteriousness has a broad definition and that the methods and systems described herein may be applied to deleteriousness labels, but also to labels of related or other kinds.

More generally, labels represent additional information that should be associated between variants of similar function. Labels may be categorical, with two values, such as "yes" and "no", or "damaging" and "non-damaging", or may have one of more than two values, such as "benign", "likely benign", "likely pathogenic", "pathogenic" and "uncertain significance". Labels may real-valued, such as a real number between zero and one where zero corresponds to low pathogenicity and one corresponds to high pathogenicity. Labels may be scores with numeric values that indicate how deleterious, pathogenic, or damaging variants are expected to be. The labels may reflect other quantitative aspects of gross phenotype, phenotype or molecular phenotype, such as those associated with diabetes, cardiovascular conditions and neurological disorders. An example is the IQ coefficient. Labels may be vector-valued; for example, three quantitative phenotypes can be encoded as a vector of length 3, (value 1, value 2, value 3). Categorical labels may be encoded as vectors using one-hot encoding. For example, the categories "benign", "likely benign", "likely pathogenic" and "pathogenic" can be encoded as the vector labels (1,0,0,0), (0,1,0,0), (0,0,1,0) and (0,0,0,1). It will be appreciated that labels may be encoded in different ways and that the systems and methods described herein can be applied.

Figure 7:
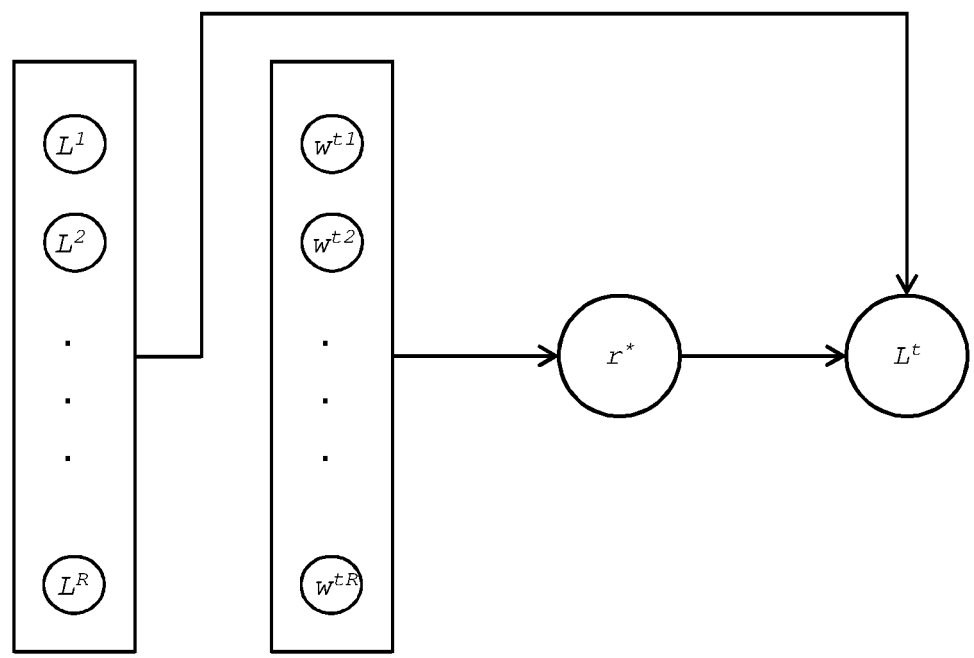
FIG. 7 is a block diagram illustrating labeling of variants.

Referring now to FIG. 7, labels for deleteriousness may be associated with some variants and these labeled variants may be used to determine labels for other variants. Denote the label for variant r by $L^r$. The label may be a one-hot encoding of a classification, such as where a label of (1,0) indicates that the variant is not deleterious and a label of (0,1) indicates that the variant is deleterious. The label may be real-valued, such as a real number between 0 and 1, where 0 indicates that the variant is not deleterious and 1 indicates that it is deleterious. It is appreciated that other categorical, numerical, or vector-numerical labels may be used. The labels of the other variants indexed by t may be determined using the labeled variant with lowest link distance, with the formula:

$$L^t \leftarrow L^{r^*},$$

where $r^*$ is selected such that $d^{tr^*} \leq d^{tr}$ for all labeled variants r.

Figure 8:
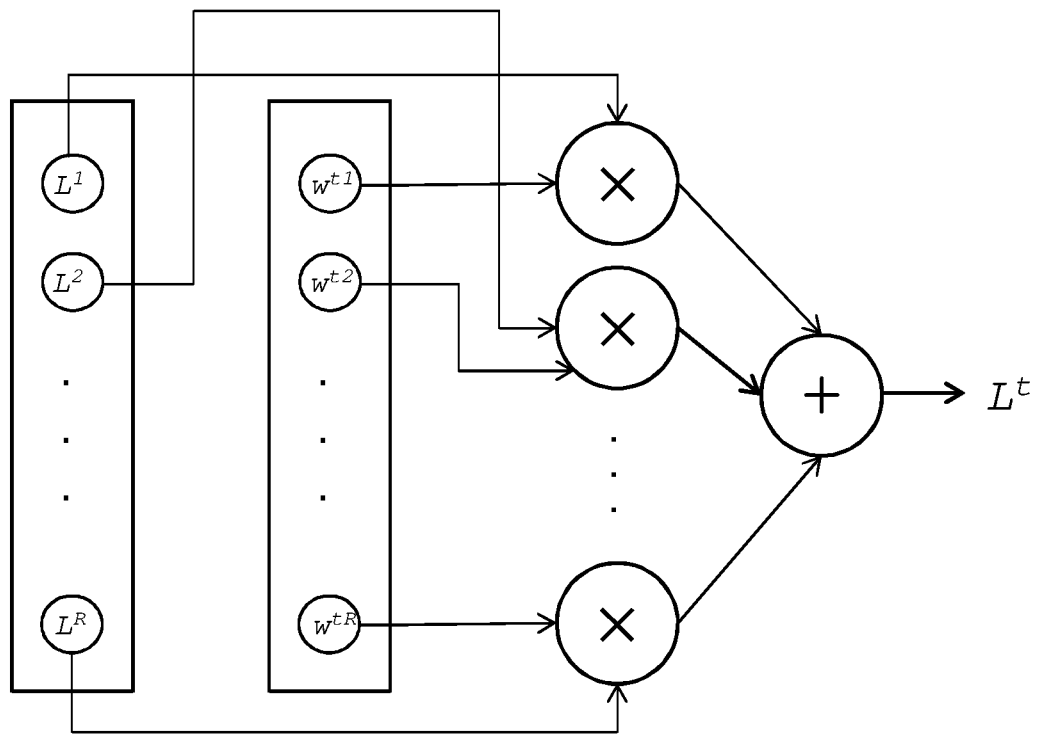
FIG. 8 is a block diagram illustrating weighting for labeling of variants.
Figure 9:
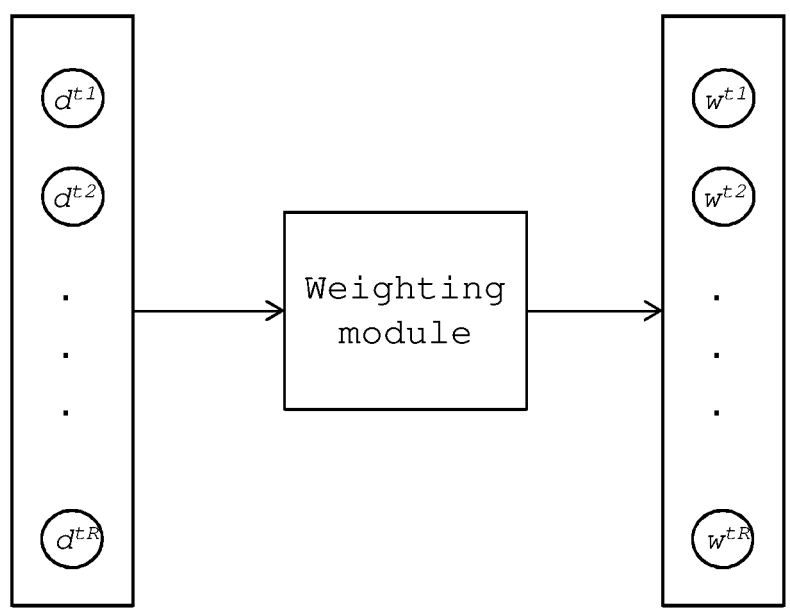
FIG. 9 is a block diagram illustrating the determination of weights used for weighting for labeling of variants.

Referring now to FIG. 8, the labels for the other variants may be determined by a weighted average of the labels of the labeled variants. Referring now to FIG. 9, for another variant t, a weighting module is applied to determine the weights for all labeled variants and then the weights are used to combine the labels of the labeled variants:

$$L^t \leftarrow \sum_{r=1}^{R} w^{tr} L^r.$$

This weighted combination of labels requires that the labels be represented numerically, such as using one-hot encoding. It will be appreciated that other numerical encodings of labels are possible and that the label may represent a continuous quantity, such as a probability distribution or a real-valued pathogenicity level.

Referring now to FIG. 9, the weighting module takes as input link distances and outputs a set of weights. Denote the weight for the other variant t and the labeled variant r by $w^{tr}$. The weights are determined by applying a linear or a nonlinear weighting module to the link distances:

$$(w^{t1}, w^{t2}, \ldots, w^{tR}) \leftarrow f(d^{t1}, d^{t2}, \ldots, d^{tR}),$$

where $f( )$ is the result of the linear or nonlinear weighting module and the labeled variants are indexed by $1, \ldots, R$.

The weighting module may determine the weights for different labeled variants independently:

$$(w^{t1}, w^{t2}, \ldots, w^{tR}) \leftarrow (f'(d^{t1}), f'(d^{t2}), \ldots, f'(d^{tR})),$$

where $f'( )$ is the result of the weighting module applied to each link distance individually. This corresponds to a weighting module with the following form:

$$f(d^{t1}, d^{t2}, \ldots, d^{tR}) = (f'(d^{t1}), f'(d^{t2}), \ldots, f'(d^{tR})).$$

Examples of such weighting modules $f'( )$ include:

$$f'(d^{tr}) \leftarrow 1/(1+\alpha d^{tr}),$$

$$f'(d^{tr}) \leftarrow \exp(-\alpha d^{tr}),$$

$$f'(d^{tr}) \leftarrow 1/(1+\exp(\alpha(d_0 - d^{tr}))),$$

where $\alpha$ and $d_0$ are predetermined numerical parameters. $\alpha$ determines how quickly the magnitude of the weight drops off when the link distance increases. The first two formulas cause the weight to drop immediately when the link distance increases from zero. The third formula allows for the weight to drop off only when it starts to approach a threshold on the link distance, $d_0$. It will be appreciated that other nonlinear weighting functions may be used.

Figure 10:
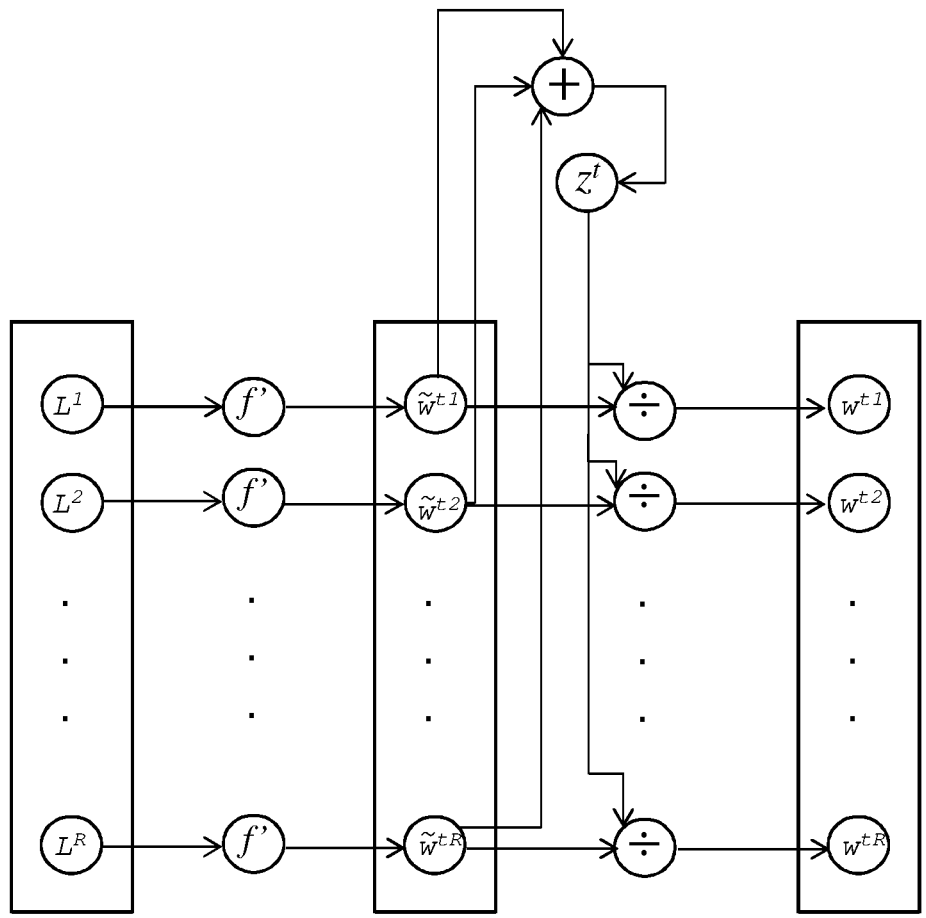
FIG. 10 is a second block diagram illustrating the determination of weights used for weighting for labeling of variants.

Referring now to FIG. 10, the weighting module may determine the weights for different labeled variants in a way that depends on more than one labeled variant. For example, the weights for one other variant and all labeled variants may be normalized so that the sum over the labeled variants is one. The weighting module first computes the un-normalized weights independently for different labeled variants:

$$\tilde{w} \leftarrow f'(d^{tr}), \text{ for } r=1, \ldots, R.$$

Then, the weighting module determines the normalization factor:

$$z^t = \sum_{r=1}^{R} \tilde{w}^{tr}.$$

Lastly, the weighting module outputs the normalized weights:

$$(w^{t1}, w^{t2}, \ldots, w^{tR}) \leftarrow (\tilde{w}^{t1}/z^t, \tilde{w}^{t2}/z^t, \ldots, \tilde{w}^{tR}/z^t)$$

It will be appreciated that these computations can be performed differently so as to achieve the same or a very similar effect.

Another example of a weighting module that determines the weights for different labeled variants in a way that depends on more than one labeled variant, is a weighting module that places all weight on the labeled variant with the lowest link distance. The weighting module first identifies the labeled variant with lowest link distance:

$$r^* \leftarrow \arg\min_r d^{tr},$$

Then, it sets the corresponding weight to one and the others to zero:

$$(w^{t1}, w^{t2}, \ldots, w^{tR}) \leftarrow ([r^*=1], [r^*=2], \ldots, [r^*=R]),$$

where [ ] indicates Iverson's notation, as described above. It will be appreciated that the set of weights may be determined efficiently by setting all weights to zero and then setting the weight for label $r^*$ to one.

After the weights are computed, the label of the other variant t may be determined by combining the labels of the labeled variants, using the weights:

$$L^t \leftarrow \sum_{r=1}^{R} w^{tr} L^r.$$

It will be appreciated that labeled variants that have a weight of zero need not be explicitly multiplied by their weights and summed over:

$$L^t \leftarrow \sum_{r \in (1, \ldots, R), w^{tr} \neq 0} w^{tr} L^r.$$

In the case of picking the labeled variant with lowest link distance, this summation reduces to $$L^t \leftarrow L^{r^*}.$$

Another example of a weighting module that determines the weights for different labeled variants in a way that depends on more than one labeled variant, is a weighting module that outputs equal weights on the $\rho$ labeled variants that have lowest link distance.

The weighting module parameters, such as $\alpha$, $\rho$, $d_0$ may be set by hand or by searching over appropriate values using a dataset of variants with known labels, such as to obtain the highest possible correct label classification rate.

The labels may be encoded as real-valued or binary-valued vectors, in which case the weighted combination of labels will result in a vector label of the same length. If the reference variant labels use a one-hot encoding, such as where a label of (1,0) indicates that the variant is not deleterious and a label of (0,1) indicates that the variant is deleterious, the weighted combination of the labels of the labeled variants will result in a real-valued vector. For example, if the normalized weights for 5 labeled variants are 0.5, 0.3, 0.1, 0.1, 0.0 and the labeled variants have labels (0,1), (0,1), (1,0), (1,0), (1,0), then the label of the other variant will be 0.5×(0,1)+0.3×(0,1)+0.1×(1,0)+0.1×(1,0)+0.0×(1,0), which equals (0.2,0.8), indicating that the label (0,1) has more evidence than the label (1.0), but that there is some uncertainty. It will be appreciated that this is a small example and that in practical applications the number of variants may be higher, such as in the thousands, in the millions or even higher.

Once the labels have been determined for a set of other variants indexed from 1 to τ, the other variants may be prioritized by sorting their labels. If the labels use a one-hot encoding, such as where a label of (1,0) indicates that the variant is not deleterious and a label of (0,1) indicates that the variant is deleterious, the second label value for each other variant may be used for prioritization. For example, if there are 4 other variants with labels (0.2,0.8), (0.7,0.3), (0.1,0.9), (0.9,0.1) corresponding to other variants 1, 2, 3 and 4, and we use the second label value, which corresponds to the deleterious label, we will prioritize the 4 other variants using the values 0.8, 0.3, 0.9 and 0.1. Sorting this list of values gives us a prioritized list of other variants: 3, 1, 2, 4, that is, other variant 3 is the "most deleterious" and other variant 4 is the "least deleterious". The other variants prioritized in this way may be subject to subsequent analysis, which may include further computational analysis or experimental analysis. It will be appreciated that the other variants may be prioritized in different ways using the labels.

The weights used to combine the labels of the labelled variants can be constructed so as to have different values for different possible values of the labels. This can be used to correct for different link distance densities of labeled variants, for example, wherein the number of variants labeled benign is significantly higher than the number of variants labeled pathogenic. Denote the label vector length by v, so that the label of the labeled variant $L^r$ can be represented as $$L^r = (L_1^r, L_2^r, \ldots, L_v^r).$$

An example is label that uses a one-hot encoding, where $L^r$ is a binary vector with a 1 in one position and zero everywhere else. The weight $w^{tr}$ for the other variant t and the labeled variant r can be a real-valued vector of the same length, v:

$$w^{tr} = (w_1^{tr}, w_2^{tr}, \ldots, w_v^{tr}).$$

The weights are determined by applying a weighting module to the link distances, in a way so that different possible values of the labels may have different weights. Using e to index the labels such that e ranges from 1 to v, the weighting module may determining the weights as follows:

$$w_e^{tr} \leftarrow 1/(1 + \alpha_e d^{tr}),$$

$$w_e^{tr} \leftarrow \exp(-\alpha_e d^{tr}),$$

$$w_e^{tr} \leftarrow \left(\frac{1}{1 + \exp(\alpha_e(d_{0,e} - d^{tr}))}\right),$$

where $\alpha_e$ and $d_{0,e}$ are predetermined numerical parameters that determine how quickly the weights drop off to zero as link distance increases, but in a way that is label dependent. For instance, if the labels are (1,0) for "benign" and (0,1) for "pathogenic" and, for a particular test variant, the link distance density of labeled benign variants is much larger than the density of labeled pathogenic variants nearby in the genome, then we can set $\alpha_1$ and $\alpha_2$ to values such that the weights drop off more quickly with link distance for the benign variants: $\alpha_1 > \alpha_2$. The weights for each label value $e=1, \ldots, q$ may be separately normalized so that the sum over the labeled variants is one. The weighting module first computes the un-normalized weights $\tilde{w}_e^{tr}$ independently for different labeled variants, such as by using $$\tilde{w}_e^{tr} \leftarrow 1/(1 + \alpha_e d^{tr}).$$

Then, for each label value, the weighting module determines the normalization factor:

$$z_e^t = \sum_{r=1}^R \tilde{w}_e^{tr'} \text{ for } e=1 \ldots q.$$

Lastly, the weighting module outputs the normalized weights:

$$(w_1^{t1}, w_1^{t2}, \ldots, w_1^{tR}) \leftarrow (\tilde{w}_1^{t1}/z_1^t, \tilde{w}_1^{t2}/z_1^t, \ldots, \tilde{w}_1^{tR}/z_1^t).$$

$$(w_q^{t1}, w_q^{t2}, \ldots, w_q^{tR}) \leftarrow (\tilde{w}_q^{t1}/z_q^t, \tilde{w}_q^{t2}/z_q^t, \ldots, \tilde{w}_q^{tR}/z_q^t).$$

It will be appreciated that these computations can be performed differently so as to achieve the same or a very similar effect.

For all label values $e=1, \ldots, q$, the eth label of the other variant t may be determined using the weighted average:

$$L_e^t \leftarrow \sum_{r=1}^R w_e^{tr} L_e^r.$$

The weighting module parameters may be set by hand or by searching over appropriate values using a dataset of variants with known labels, such as to obtain the highest possible correct label classification rate.

The link distance provides information about how similar two variants are in their molecular phenotype, but additional information may be available about the variants that can be used by the weighting module to determine the weights. Additional information may include the proximity of the two variants within the biological sequence, such as the difference in the coordinates of two single-substitution variants; quantitative trait loci information, such as expression- or splicing-quantitative trait loci information; information about the linkage disequilibrium between the two variants or between the two variants and other variants of interest; information pertaining to other information for variants that are implicated in a specific disease or class of diseases. It will be appreciated that other types of information may be used to adjust the weights. We denote this additional information for other variant t and labeled variant r by $l^{tr}$.

More generally, the link distance may be determined using a link neural network, which takes as input the molecular phenotype of the labeled variant for contexts $c=1, \ldots, T$, $m^r = (m_1^r, \ldots, m_T^r)$, and the molecular phenotype of the other variant for contexts $c=1, \ldots, T$, $m^t = (m_1^r, \ldots, m_T^r)$, and the additional information $l^{tr}$, and outputs the link distance $d^{tr}$. Denoting the operations of the link neural network by N( ), the application of the link neural network can be represented as $$d^{tr} \leftarrow N(m^t, m^r, l^{tr}).$$

The parameters of the link neural network may be determined from a dataset of examples, wherein each example consists of the pair of variants, the additional information, and the target, which may be derived from labels for the variants and a measure of similarity on the labels. An appropriate machine learning method can be used to configure the link neural network.

In one embodiment, the link neural network is not trained using a dataset of examples, but is instead configured by hand. For example, if the link neural network is configured as follows, $$N(m^t, m^r, l^{tr}) \leftarrow \sum_{c=1}^T (m_c^t - m_c^r)^2,$$

then it acts to produce the link distance described above.

In another embodiment, the additional information pertains to the proximity of two localized variants, such as single-substitution variants, within the biological sequence. In this case, for one of the other variants, the labeled variants that are nearby in the biological sequence may be given lower link distances, even if their molecular phenotypes are similar. Denote the absolute difference in coordinates between the other variant t and the labeled variant r in the biological sequence by $l^{tr}$. If this value is large, the variants are less likely to have similar function, all else being the same, than if the value is small. The link neural network may be configured as follows:

$$N(m^t, m^r, l^{tr}) \leftarrow \sum_{c=1}^T (m_c^t - m_c^r)^2 + \gamma l^{tr},$$

where γ is a parameter that trades off the effect of the molecular phenotype distance and the additional information. This parameter may be set using training data. It will be appreciated that other measures of proximity may be used, such as square differences in coordinates, and that other types of additional information may be used. It will be appreciated that multiple types of additional information may be encoded in $l^{tr}$, including real-valued, vector-valued and categorical information, which may be encoded, for instance, using one-hot encoding.

Although the invention has been described with reference to certain specific embodiments, various modifications thereof will be apparent to those skilled in the art without departing from the spirit and scope of the invention as outlined in the claims appended hereto.

The invention claimed is:

1. A system for determining numerical link distances between two or more biologically related variants, comprising:
one or more trained molecular phenotype neural networks (MPNNs), each of the one or more trained MPNNs comprising:
an input layer of a neural network, the input layer obtaining one or more input values digitally representing a variant of the two or more biologically related variants, wherein each of the two or more biologically related variants is derived from a biological sequence through a combination of substitutions, insertions, or deletions to the biological sequence, wherein the biological sequence is a deoxyribonucleic acid (DNA) sequence, a ribonucleic acid (RNA) sequence, or a protein sequence;
one or more feature detectors of the neural network, each feature detector of the one or more feature detectors obtaining input values from (i) one or more of the input values in the input layer, or (ii) an output value of another feature detector of the one or more feature detectors;
an output layer of the neural network, the output layer comprising one or more output values representing a molecular phenotype for the variant, the one or more output values comprising one or more numerical elements obtained from the one or more feature detectors, wherein the molecular phenotype comprises numerical elements which quantify biological molecules of cells; and
a comparator obtaining the one or more output values of the output layer of each of the one or more trained MPNNs, the comparator determining a numerical link distance for pairs of variants of the two or more biologically related variants based at least in part on a difference between the numerical elements of the molecular phenotypes for the pairs of variants.

2. The system of claim 1, further comprising an encoder generating the one or more input values, the input layer obtaining the one or more input values from the encoder.

3. The system of claim 2, wherein the one or more input values correspond to an encoded representation of one or more contexts.

4. The system of claim 1, wherein the input layer further obtains an additional one or more values digitally representing one or more contexts, and wherein the molecular phenotype further comprises numerical elements for at least one of the one or more contexts.

5. The system of claim 1, wherein the comparator determines the numerical link distance for a pair of variants at least in part by applying a function to the difference between the numerical elements of the molecular phenotypes for the pair of variants, wherein the function is selected from the group consisting of an identity function, a square function, and an absolute value function.

6. The system of claim 1, wherein at least one of the two or more biologically related variants comprises:
a. a DNA sequence, an RNA sequence, or a protein sequence from an individual;
b. a DNA sequence, an RNA sequence, or a protein sequence which is modified by applying a DNA editing system, an RNA editing system, or a protein modification system;
c. a DNA sequence, an RNA sequence, or a protein sequence which is modified by setting one or more nucleotides which are targeted by a therapy to fixed nucleotide values;
d. a DNA sequence, an RNA sequence, or a protein sequence which is modified by setting one or more nucleotides which are targeted by a therapy to values different from existing nucleotide values; or
e. a DNA sequence, an RNA sequence, or a protein sequence which is modified by deleting one or more nucleotides which overlap with nucleotides that are targeted by a therapy.

7. The system of claim 1, wherein the molecular phenotype comprises one or more numerical elements selected from the group consisting of: a percentage of transcripts that include an exon; a percentage of transcripts that use an alternative splice site; a percentage of transcripts that use an alternative polyadenylation site; an affinity of an RNA-protein interaction; an affinity of a DNA-protein interaction; a specificity of a microRNA-RNA interaction; and a level of protein phosphorylation.

8. The system of claim 1, wherein one or more variants of the two or more biologically related variants are labeled variants, wherein the labeled variants have associated labels, and wherein the system further comprises a labeling unit, wherein the labeling unit obtains the numerical link distances for the pairs of variants of the two or more biologically related variants from the comparator, and associates labels with unlabeled variants of the two or more biologically related variants based at least in part on the numerical link distances.

9. The system of claim 8, wherein the labeling unit further associates each of the unlabeled variants with the associated label of the labeled variant of the labeled variants having a smallest numerical link distance to the unlabeled variant.

10. The system of claim 8, wherein for each of the unlabeled variants, the one or more trained MPNNs further determine for each of the labeled variants, a numerical weight for the unlabeled variant and the labeled variant by applying a weighting module to the numerical link distance between the unlabeled variant and the labeled variant, and wherein the labeling unit further determines an associated label for the unlabeled variant by summing terms corresponding to the labeled variants, wherein each of the terms is obtained by multiplying the numerical weight for the unlabeled variant and the corresponding labeled variant into the associated label for the corresponding labeled variant.

11. The system of claim 1, wherein the comparator further determines, for each of one or more pairs of variants in the two or more biologically related variants, a measure of proximity of the pair of variants within the biological sequence, and wherein the comparator determines the numerical link distance at least in part by processing the measure of proximity of the pair of variants with the numerical elements of the molecular phenotypes for the pair of variants.

12. The system of claim 1, wherein the comparator determines the numerical link distance at least in part by:
   using a trained link neural network to process the numerical elements of the molecular phenotypes for a pair of variants to determine the numerical link distance for the pair of variants.

13. A computer-implemented method for determining numerical link distances between two or more biologically related variants, comprising:
   a. obtaining at an input layer of a trained molecular phenotype neural network (MPNN), one or more input values digitally representing a variant of the two or more biologically related variants, wherein each of the two or more biologically related variants is derived from a biological sequence through a combination of substitutions, insertions, or deletions to the biological sequence, wherein the biological sequence is a deoxyribonucleic acid (DNA) sequence, a ribonucleic acid (RNA) sequence, or a protein sequence;
   b. processing the one or more input values by the trained MPNN, the trained MPNN comprising one or more feature detectors obtaining input values from (i) the one or more of the input values in the input layer, or (ii) an output value of another feature detector of the one or more feature detectors, the MPNN generating one or more output values representing a molecular phenotype for the variant, the one or more output values comprising one or more numerical elements obtained from the one or more feature detectors, wherein the molecular phenotype comprises numerical elements which quantify biological molecules of cells; and
   c. determining, by a comparator, a numerical link distance for pairs of variants of the two or more biologically related variants based at least in part on a difference between the numerical elements of the molecular phenotypes for the pairs of variants.

14. The method of claim 13, further comprising using an encoder to generate the one or more input values, and using the input layer to obtain the one or more input values from the encoder.

15. The method of claim 14, wherein the one or more input values correspond to an encoded representation of one or more contexts.

16. The method of claim 13, further comprising using the input layer to obtain an additional one or more values digitally representing one or more contexts, wherein the molecular phenotype further comprises numerical elements for at least one of the one or more contexts.

17. The method of claim 13, further comprising using the comparator to determine the numerical link distance for a pair of variants at least in part by applying a function to the difference between the numerical elements of the molecular phenotypes for the pair of variants, wherein the function is selected from the group consisting of an identity function, a square function, and an absolute value function.

18. The method of claim 13, wherein at least one of the two or more biologically related variants comprises:
   a. a DNA sequence, an RNA sequence, or a protein sequence from an individual;
   b. a DNA sequence, an RNA sequence, or a protein sequence which is modified by applying a DNA editing system, an RNA editing system, or a protein modification system;
   c. a DNA sequence, an RNA sequence, or a protein sequence which is modified by setting one or more nucleotides which are targeted by a therapy to fixed nucleotide values;
   d. a DNA sequence, an RNA sequence, or a protein sequence which is modified by setting one or more nucleotides which are targeted by a therapy to values different from existing nucleotide values; or
   e. a DNA sequence, an RNA sequence, or a protein sequence which is modified by deleting one or more nucleotides which overlap with nucleotides that are targeted by a therapy.

19. The method of claim 13, wherein the molecular phenotype comprises one or more numerical elements selected from the group consisting of: a percentage of transcripts that include an exon; a percentage of transcripts that use an alternative splice site; a percentage of transcripts that use an alternative polyadenylation site; an affinity of an RNA-protein interaction; an affinity of a DNA-protein interaction; a specificity of a microRNA-RNA interaction; and a level of protein phosphorylation.

20. The method of claim 13, wherein one or more variants of the two or more biologically related variants are labeled variants, wherein the labeled variants have associated labels, and wherein the method further comprises using a labeling unit to obtain the numerical link distances for the pairs of variants of the two or more biologically related variants from the comparator, and associate labels with unlabeled variants of the two or more biologically related variants based at least in part on the numerical link distances.

21. The method of claim 20, further comprising associating each of the unlabeled variants with the associated label of the labeled variant of the labeled variants having a smallest numerical link distance to the unlabeled variant.

22. The method of claim 20, further comprising, for each of the unlabeled variants and for each of the labeled variants, determining a numerical weight for the unlabeled variant and the labeled variant by applying a weighting module to the numerical link distance between the unlabeled variant and the labeled variant; and determining an associated label for the unlabeled variant by summing terms corresponding to the labeled variants, wherein each of the terms is obtained by multiplying the numerical weight for the unlabeled variant and the corresponding labeled variant into the associated label for the corresponding labeled variant.

23. The method of claim 13, further comprising using the comparator to determine, for each of one or more pairs of variants in the two or more biologically related variants, a measure of proximity of the pair of variants within the biological sequence, wherein the numerical link distance is determined at least in part by processing the measure of proximity of the pair of variants with the numerical elements of the molecular phenotypes for the pair of variants.

24. The method of claim 13, further comprising using the comparator to determine the numerical link distance at least in part by:
   using a trained link neural network to process the numerical elements of the molecular phenotypes for a pair of variants to determine the numerical link distance for the pair of variants.

* * * * *